United States Patent
Sugino et al.

(10) Patent No.: US 9,518,292 B2
(45) Date of Patent: Dec. 13, 2016

(54) METHODS FOR SUPPRESSION PCR

(75) Inventors: Ken Sugino, Ashburn, VA (US); Serena David, Marlborough, MA (US); Saori Kato, Seto (JP); Sean O'Toole, Somerville, MA (US); Sacha Nelson, Weston, MA (US)

(73) Assignee: BRANDEIS UNIVERSITY, Waltham, MA (US)

( * ) Notice: Subject to any disclaimer, the term of this patent is extended or adjusted under 35 U.S.C. 154(b) by 196 days.

(21) Appl. No.: 14/119,471

(22) PCT Filed: May 25, 2012

(86) PCT No.: PCT/US2012/039609
§ 371 (c)(1),
(2), (4) Date: Jul. 10, 2014

(87) PCT Pub. No.: WO2012/162621
PCT Pub. Date: Nov. 29, 2012

(65) Prior Publication Data
US 2014/0315211 A1  Oct. 23, 2014

Related U.S. Application Data

(60) Provisional application No. 61/490,341, filed on May 26, 2011.

(51) Int. Cl.
*C12Q 1/68* (2006.01)
*C12P 19/34* (2006.01)

(52) U.S. Cl.
CPC ............. *C12Q 1/686* (2013.01); *C12Q 1/6858* (2013.01)

(58) Field of Classification Search
None
See application file for complete search history.

(56) References Cited

U.S. PATENT DOCUMENTS

| 7,618,773 | B2 | 11/2009 | Rand et al. | |
| 8,815,515 | B1 * | 8/2014 | Zhou | C12Q 1/686 435/6.1 |

FOREIGN PATENT DOCUMENTS

| CA | 2693384 | 2/2009 |
| EP | 2272952 | 1/2011 |

OTHER PUBLICATIONS

Zhou et al., "Snapback primer Genotyping with Saturating DNA Dye and Melting Analysis," Clinical Chemistry, 2008, vol. 54, No. 10, pp. 1648-1656.*

(Continued)

*Primary Examiner* — Young J Kim
(74) *Attorney, Agent, or Firm* — Nixon Peabody LLP; Ronald I. Eisenstein

(57) ABSTRACT

Provided herein are approaches for the detection, identification, and/or selective amplification of specific target species or target variants of nucleic acid sequences, even within an excess of unwanted similar sequences or variants. These approaches include methods, assays, and kits for suppression PCR that require, in part, DNA polymerase that lacks 5'-3' exonuclease activity, and a PCR primer, termed a forward selective primer or a nunchaku primer. The methods, assays, and kits provided herein are useful for a wide variety of applications, including cancer screening assays and kits, personalized screening assays, SNP (single nucleotide polymorphism) genotyping and identification, and downstream applications such as next generation high-throughput genomic sequencing and library construction.

17 Claims, 10 Drawing Sheets

(56) References Cited

OTHER PUBLICATIONS

Rand et al., "Headloop suppression PCR and its application to selective amplification of methlylated DNA sequences", Nucl. Acids Res. 33(14):e127 (2005).

* cited by examiner

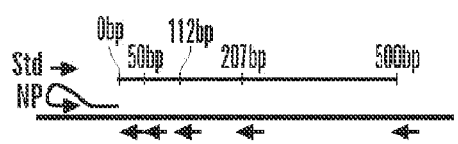
*FIG. 3A*
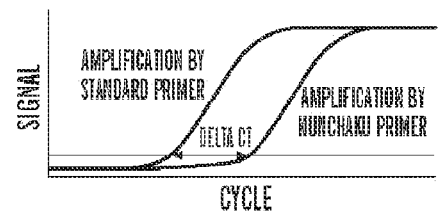
*FIG. 3B*
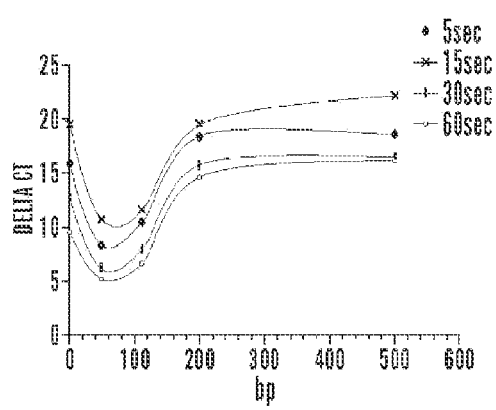
*FIG. 3C*
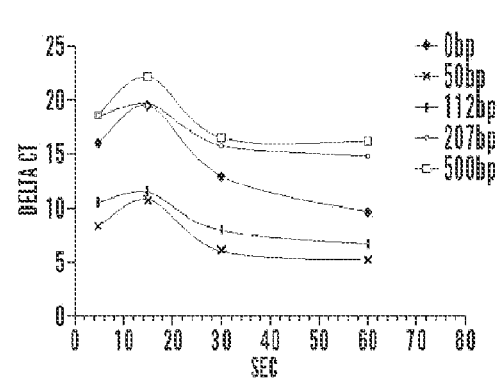
*FIG. 3D*
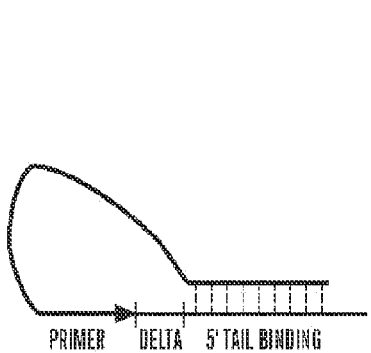
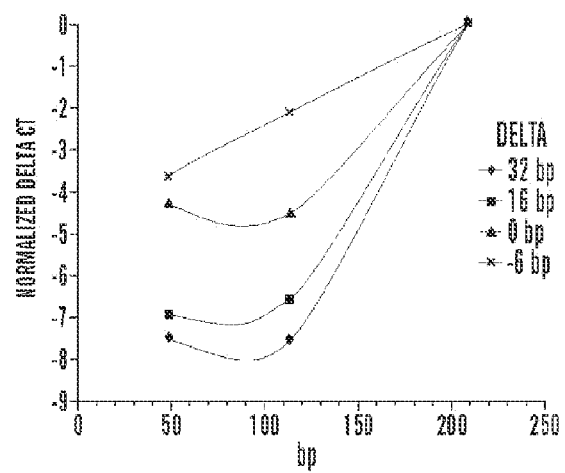
*FIG. 4*

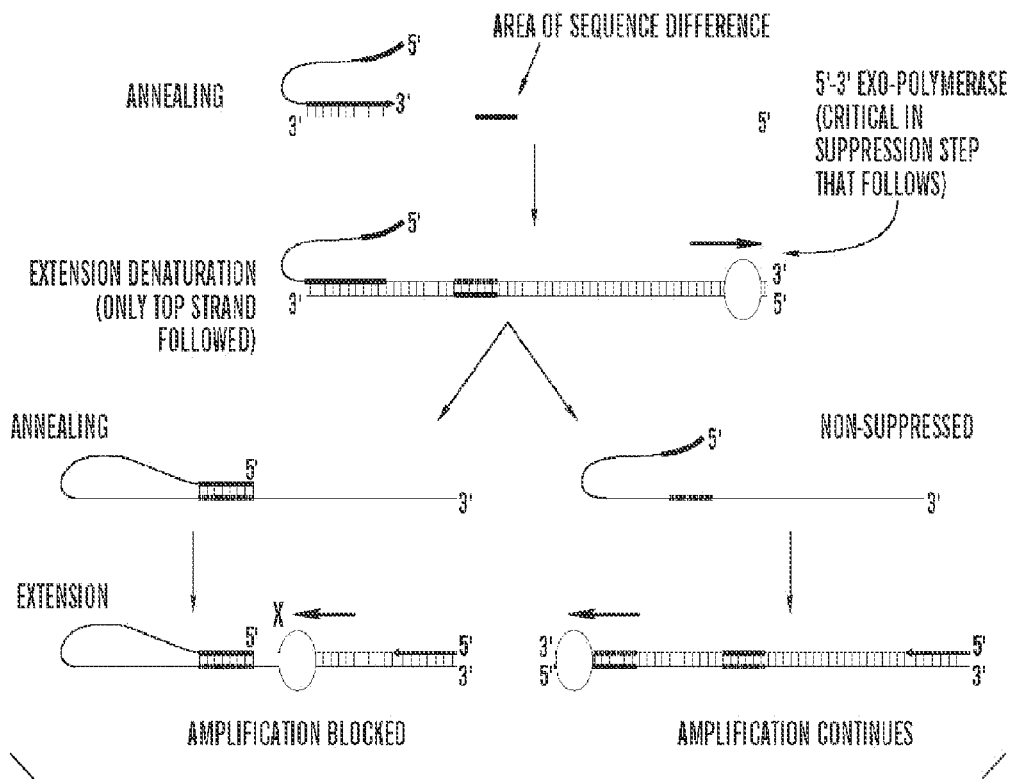

FIG. 13

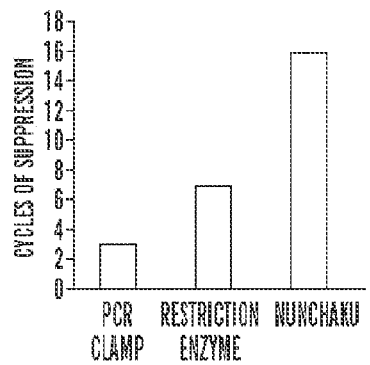

- NUNCHAKU vs. PCR CLAMP
  - NO 3rd OLIGO WITH EXPENSIVE 3' - MODIFICATION
  - IMPROVED KINETICS - UNIMOLECULAR RATHER THAN BIMOLECULAR INTERACTION

- NUNCHAKU vs. RESTRICTION ENZYME
  - NO RESTRICTION ENZYME - IMPROVED PROCESS FLEXIBILITY AND COST
  - NO NEED FOR NEARBY RESTRICTION ENZYME SITE - IMPROVED APPLICABILITY

| TECHNIQUE | EQUIVALENT CYCLES OF SUPPRESSION | SUPPRESSION FACTOR |
|---|---|---|
| PCR CLAMP | 3 | 8 |
| RESTRICTION ENZYME | 7 | $2^7 \sim 120$ |
| NUNCHAKU | 16 | $2^{16} \sim 65,000$ |

FIG. 14

METHODS FOR SUPPRESSION PCR

CROSS-REFERENCE TO RELATED APPLICATIONS

This application is a 35 U.S.C. §371 National Phase Entry Application of International Application No. PCT/US2012/039609 filed May 25, 2012, which designates the U.S., and which claims benefit under 35 U.S.C. §119(e) of U.S. Provisional Application No. 61/490,341 filed on May 26, 2011, the contents of each of which are incorporated herein by reference in their entireties.

GOVERNMENT SUPPORT

The invention was made with Government support under Grant No.: 5U01 MH07884425910310 awarded by the National Institutes of Health. The Government has certain rights in the invention.

FIELD OF THE INVENTION

The invention generally relates PCR methods for the selective detection, identification, and/or amplification of target sequences. Various embodiments relate to the suppression of amplification of closely related non-amplification target sequences in the same reaction with amplification target sequences.

BACKGROUND

The polymerase chain reaction (PCR) is based on repeated cycles of denaturation of double stranded DNA, followed by oligonucleotide primer annealing to the DNA template, and primer extension by a DNA polymerase (e.g., see Mullis et al U.S. Pat. Nos. 4,683,195, 4,683,202 and 4,800,159). The oligonucleotide primers used in PCR are designed to anneal to opposite strands of the DNA, and are positioned so that the DNA polymerase-catalysed extension product of one primer can serve as a template strand for the other primer. The PCR amplification process results in the exponential increase of discrete DNA the length of which is defined by the 5' ends of the oligonucleotide primers. Specificity in standard PCR, amplification of DNA is principally determined by the sequence of the primers in combination with the temperature at which the annealing step is conducted. For closely related sequences, additional approaches have been incorporated to provide selective amplification. PCR performed with standard primers cannot distinguish one sequence from a closely related sequence if the primers used can bind to both sequences to generate an extension substrate. U.S. Pat. No. 7,618,773 and Rand et al., Nucl. Acids Res. 33:e127 (2005) describe a "headloop" suppression PCR method taught to suppress amplification of non-amplification target variants by extension of a 3' stem-loop to form a hairpin structure that can no longer provide a template for further amplification.

SUMMARY OF THE INVENTION

Described herein are novel approaches for the detection, identification, and/or selective amplification of specific target species or target variants of nucleic acid sequences, even within an excess of unwanted similar sequences or variants. Accordingly, the approaches described herein provide methods and assays for selectively amplifying and/or quantifying a target nucleic acid variant present in, or isolated from, a sample of interest, despite the presence of even a large number or quantity of similar, sequence-related non-target nucleic acid variants, which are actively suppressed using primers termed "nunchaku primers" or "forward selective primers."

Herein, we provide new methods, assays, and kits for suppression PCR with improved suppression efficiency, easier design principle, and reduced cost. The methods, assays, and kits provided require: a) using a template-specific DNA polymerase that lacks 5'-3' exonuclease activity, and b) using a PCR primer, termed herein as a "forward selective primer" or a "nunchaku primer" comprising a 5' suppression sequence or tail that is about 20-30 base pairs longer than a normal primer. Therefore, the costs of the tail-loop suppression assays described herein are almost equivalent to that of a standard PCR assay. Moreover, designing of the forward selective primer is easy and robust, unlike other suppression PCR methods in which the melting temperatures of the primers have to be carefully adjusted.

The suppression PCR methods, assays, and kits described herein require two things: (1) a tail sequence or 5' suppression sequence added at the 5' end of a forward primer (termed herein the "forward selective primer"), the tail designed to include sequence substantially identical to a portion the sequence(s) desired to be suppressed (the "suppression target sequences"), and (2) the use of polymerase lacking 5' to 3' exonuclease activity, i.e., a 5' to 3' exonuclease minus polymerase. The primer with tail, termed herein a forward selective primer or nunchaku primer, first anneals to any sequences comprising a forward selective primer binding site, and gets extended to form a first synthesized strand, referred to herein as the complementary extension sequence. After denaturation, during the subsequent annealing and extension phases, the sequence(s) desired to be suppressed will hybridize to the complementary sequence in the 5' suppression sequence or 5' tail and form a stem loop. The sequence to be amplified and not suppressed, termed the amplification target nucleic acid sequence, will not form this loop because it lacks sequence complementary to the suppression sequence in the tail. When the polymerase lacking 5' to 3' polymerase activity extends from the reverse primer, which is designed to bind to a sequence shared by all complementary extension sequences generated, it is blocked at the stem loop formed for complementary extension sequences generated from suppression target sequences, but won't be blocked for complementary extension sequences generated from the amplification target nucleic acid sequence (see, for example, FIG. 1 or 13). As described herein, we have found that these methods provide selective amplification down to sequences that vary by a single nucleotide. In some embodiments, such as when detecting small deletions, the methods, assays, and kits described herein can easily be used to overcome million-fold or more excesses of closely related sequences not desired to be amplified.

Accordingly, provided herein, in some aspects, are methods of detecting the presence of one of two or more variants of a target nucleic acid sequence in a nucleic acid sample. In some aspects, the methods comprise:

(a) hybridizing a forward selective primer to a nucleic acid sample comprising an amplification target sequence and a suppression target sequence, where the forward selective primer comprises: (i) a 3' end priming sequence that is fully complementary and hybridizes to a portion of the amplification target sequence and the at least one suppression target sequence, and (ii) a 5' end suppression sequence that is substantially identical to a portion of the suppression target sequence, wherein the portion of the suppression target to which the 5' suppression sequence is substantially identical is 5' of the portion of the suppression target sequence to which the 3' end priming sequence hybridizes;

(b) extending the hybridized forward selective primer of step (a) using a 5' to 3' polymerase enzyme that lacks 5' to 3' exonuclease activity, the extension generating hybridized duplexes comprising: (i) the amplification target sequence and a hybridized complementary extension sequence, wherein the complementary extension sequence comprises, in the 5' to 3' direction, the forward selective primer and a sequence complementary to the amplification target sequence, and (ii) the suppression target sequence and a hybridized complementary extension sequence, wherein the complementary extension sequence comprises, in the 5' to 3' direction, the forward selective primer and a sequence complementary to the suppression target sequence;

(c) denaturing the hybridized duplexes of step (b) to separate target sequences and complementary extension sequences; and (d) hybridizing a reverse primer to the complementary extension sequences of step (c), and extending the hybridized reverse primer using a 5' to 3' polymerase that lacks 5' to 3' exonuclease activity, wherein if the complementary extension sequence comprises the sequence complementary to the suppression target sequence, then amplification is suppressed and a shorter amplification product is generated, and wherein if the complementary extension sequence comprises the sequence complementary to the amplification target sequence, then amplification is not suppressed and a longer amplification product is generated, whereby the presence of one of two or more variants of a nucleic acid sequence is detected.

Accordingly, the methods described herein allow the presence of one of two or more variants of a nucleic acid sequence to be amplified and detected.

Accordingly, provided herein, in some aspects, are methods of detecting the presence of one of two or more variants of a target nucleic acid sequence in a nucleic acid sample. In some aspects, the methods comprise:

(a) hybridizing a forward selective primer to a nucleic acid sample comprising an amplification target sequence and a suppression target sequence, where the forward selective primer comprises: (i) a 3' end priming sequence that is fully complementary and hybridizes to a portion of the amplification target sequence and the at least one suppression target sequence, and (ii) a 5' end suppression sequence that is substantially identical to a portion of the suppression target sequence, wherein the portion of the suppression target to which the 5' suppression sequence is substantially identical is 5' of the portion of the suppression target sequence to which the 3' end priming sequence hybridizes;

(b) extending the hybridized forward selective primer of step (a) using a polymerase enzyme, the extension generating hybridized duplexes comprising: (i) the amplification target sequence and a hybridized complementary extension sequence, wherein the complementary extension sequence comprises, in the 5' to 3' direction, the forward selective primer and a sequence complementary to the amplification target sequence, and (ii) the suppression target sequence and a hybridized complementary extension sequence, wherein the complementary extension sequence comprises, in the 5' to 3' direction, the forward selective primer and a sequence complementary to the suppression target sequence;

(c) denaturing the hybridized duplexes of step (b) to separate target sequences and complementary extension sequences; and (d) hybridizing a reverse primer to the complementary extension sequences of step (c), and extending the hybridized reverse primer using a 5' to 3' polymerase that lacks 5' to 3' exonuclease activity, wherein if the complementary extension sequence comprises the sequence complementary to the suppression target sequence, then amplification is suppressed and a shorter amplification product is generated, and wherein if the complementary extension sequence comprises the sequence complementary to the amplification target sequence, then amplification is not suppressed and a longer amplification product is generated, whereby the presence of one of two or more variants of a nucleic acid sequence is detected.

Accordingly, the methods described herein allow the presence of one of two or more variants of a nucleic acid sequence to be amplified and detected.

In some embodiments of these methods and all such methods described herein, the 5' to 3' polymerase that lacks 5' to 3' exonuclease activity substantially lacks strand displacement activity.

In some embodiments of these methods and all such methods described herein, steps (a)-(d) are repeated at least 10 times.

In some embodiments of these methods and all such methods described herein, the forward selective primer is at least 30 nucleotides in length.

In some embodiments of these methods and all such methods described herein, the 5' end suppression sequence is at least 10 nucleotides in length.

In some embodiments of these methods and all such methods described herein, the longer amplification product generated in step (d) is at least 40 nucleotides in length.

In some embodiments of these methods and all such methods described herein, the extending of the hybridized reverse primer using the 5' to 3' polymerase that lacks 5' to 3' exonuclease activity of step (d) occurs for at least 5 seconds or more.

In some embodiments of these methods and all such methods described herein, the forward selective primer further comprises a loop spacer sequence, where the loop sequence is 5' of the 3' end priming sequence and does not comprise a sequence complementary to the complementary extension sequences. In some embodiments, the loop spacer sequence is at least 3 nucleotides in length.

In some embodiments of these methods and all such methods described herein, the reverse primer is a reverse selective primer. In some embodiments, the reverse selective primer targets a different suppression target sequence than the forward selective primer.

In some embodiments of these methods and all such methods described herein, the nucleic acid sample is a DNA sample.

In some embodiments of these methods and all such methods described herein, the forward selective primer comprises one or more locked nucleic acids (LNAs).

In some embodiments of these methods and all such methods described herein, the 5' suppression sequence of the forward selective primer comprises one or more locked nucleic acids (LNAs).

In some embodiments of these methods and all such methods described herein, the suppression target sequence is an artifact sequence of a library construction sequence. In some embodiments, the artifact is an adapter dimer or a carrier nucleic acid attached to adapters.

Also provided herein, in some aspects, are assays for detecting the presence of one of two or more variants of a nucleic acid sequence in a nucleic acid sample, the assays comprising:

a. hybridizing a forward selective primer to a nucleic acid sample comprising an amplification target sequence and a suppression target sequence, where the forward selective primer comprises: (i) a 3' end priming sequence that is complementary to and hybridizes to a portion of the amplification target sequence and the suppression target sequence, and (ii) a 5' end suppression sequence that is substantially identical to a portion of the suppression target sequence, where the portion of the suppression target to which the 5' suppression sequence is substantially identical is 5' of the portion of the suppression target sequence to which the 3' end priming sequence hybridizes;

b. extending the hybridized forward selective primer of step (a) using a polymerase enzyme, the extension generating hybridized duplexes comprising: (i) the amplification target sequence and a hybridized complementary extension sequence, where the complementary extension sequence comprises, in the 5' to 3' direction, the forward selective primer and a sequence complementary to the amplification target sequence, and (ii) the suppression target sequence and a hybridized complementary extension sequence, where the complementary extension sequence comprises, in the 5' to 3' direction, the forward selective primer and a sequence complementary to the suppression target sequence;

c. denaturing the hybridized duplexes of step (b) to separate target sequences and complementary extension sequences; and d. hybridizing a reverse primer to the complementary extension sequences of step (c), and extending the hybridized reverse primer using a 5' to 3' polymerase that lacks 5' to 3' exonuclease activity, where if the complementary extension sequence comprises the sequence complementary to the suppression target sequence, then amplification is suppressed by formation of a stem loop by the 5' suppression sequence and a shorter amplification product is generated, and where if the complementary extension sequence comprises the sequence complementary to the amplification target sequence, then amplification is not suppressed by formation of a stem loop and a longer amplification product is generated, whereby the presence of one of two or more variants of a nucleic acid sequence is detected.

In some embodiments of these assays and all such assays described herein, steps (a)-(d) are repeated at least 10 times.

In some embodiments of these assays and all such assays described herein, the 5' to 3' polymerase that lacks 5' to 3' exonuclease activity substantially lacks strand displacement activity.

In some embodiments of these assays and all such assays described herein, the forward selective primer is at least 30 nucleotides in length.

In some embodiments of these assays and all such assays described herein, the 5' end suppression sequence is at least 10 nucleotides in length.

In some embodiments of these assays and all such assays described herein, the longer amplification product generated in step (d) is at least 40 nucleotides in length.

In some embodiments of these assays and all such assays described herein, the extending of the hybridized reverse primer using the 5' to 3' polymerase that lacks 5' to 3' exonuclease activity of step (d) occurs for at least 5 seconds or more.

In some embodiments of these assays and all such assays described herein, the forward selective primer further comprises a loop spacer sequence, where the loop spacer sequence is 5' of the 3' end priming sequence and does not comprise a sequence complementary to the complementary extension sequences.

In some embodiments of these assays and all such assays described herein, the loop spacer sequence is at least 3 nucleotides in length.

In some embodiments of these assays and all such assays described herein, the reverse primer is a reverse selective primer.

In some embodiments of these assays and all such assays described herein, the reverse selective primer targets a different suppression target sequence than the forward selective primer.

In some embodiments of these assays and all such assays described herein, the nucleic acid sample is a DNA sample.

In some embodiments of these assays and all such assays described herein, the forward selective primer comprises one or more locked nucleic acids (LNAs).

In some embodiments of these assays and all such assays described herein, the 5' suppression sequence of the forward selective primer comprises one or more locked nucleic acids (LNAs).

In some embodiments of these assays and all such assays described herein, the assay is a cancer screening assay.

In some embodiments of these assays and all such assays described herein, the assay is a personalized cancer recurrence detection assay.

In some embodiments of these assays and all such assays described herein, the amplification target sequence comprises a mutation or epigenetic modification found in cancer cells.

In some embodiments of these assays and all such assays described herein, the nucleic acid sample is obtained from a blood, serum, plasma, or urine sample.

In some embodiments of these assays and all such assays described herein, the assay is an autism screening assay.

In some embodiments of these assays and all such assays described herein, the assay is a prenatal genetic detection assay.

In some embodiments of these assays and all such assays described herein, the assay is a microbial detection assay.

In some embodiments of these assays and such assays described herein, the assay is a multiplex assay.

Also provided herein, in some aspects, are kits for detecting the presence of one of two or more variants of a nucleic acid sequence in a nucleic acid sample. Such kits comprise: at least one forward selective primer, the forward selective primer comprising: (i) a 3' end priming sequence that is fully complementary and hybridizes to a portion of an amplification target sequence and a suppression target sequence, and (ii) a 5' end suppression sequence that is substantially identical to a portion of the suppression target sequence, such that the portion of the suppression target to which the 5' suppression sequence is substantially identical is 5' of the portion of the suppression target sequence to which the 3' end priming sequence hybridizes; and instructions and packaging materials thereof.

In some embodiments of these kits and all such kits described herein, the kit further comprises a reverse primer specific for a sequence complementary to both the amplification target sequence and the suppression target sequence.

In some embodiments of these kits and all such kits described herein, the kit further comprises a reverse selective primer. In some embodiments, the reverse selective primer targets a different suppression target sequence than the forward selective primer.

In some embodiments of these kits and all such kits described herein, the kit further comprises a thermostable DNA polymerase lacking 5' to 3' exonuclease activity and substantially lacking strand displacement activity.

DEFINITIONS

For convenience, certain terms employed herein, in the specification, examples and appended claims are collected here. Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth.

Other than in the operating examples, or where otherwise indicated, all numbers expressing quantities of ingredients or reaction conditions used herein should be understood as modified in all instances by the term "about." The term "about" when used in connection with percentages can mean±1%.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in immunology, and molecular biology can be found in The Merck Manual of Diagnosis and Therapy, 18th Edition, published by Merck Research Laboratories, 2006 (ISBN 0-911910-18-2); Robert S. Porter et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006. Definitions of common terms in molecular biology are found in Benjamin Lewin, Genes IX, published by Jones & Bartlett Publishing, 2007 (ISBN-13: 9780763740634); Kendrew et al. (eds.), The Encyclopedia of Molecular Biology, published by Blackwell Science Ltd., 1994 (ISBN 0-632-02182-9); and Robert A. Meyers (ed.), Maniatis et al., Molecular Cloning: A Laboratory Manual, Cold Spring Harbor Laboratory Press, Cold Spring Harbor, N.Y., USA (1982); Sambrook et al., Molecular Cloning: A Laboratory Manual (2 ed.), Cold Spring Harbor Laboratory Press, Cold Spring Harbor, N.Y., USA (1989); Davis et al., Basic Methods in Molecular Biology, Elsevier Science Publishing, Inc., New York, USA (1986); or Methods in Enzymology: Guide to Molecular Cloning Techniques Vol. 152, S. L. Berger and A. R. Kimmerl Eds., Academic Press Inc., San Diego, USA (1987); Current Protocols in Molecular Biology (CPMB) (Fred M. Ausubel, et al. ed., John Wiley and Sons, Inc.), Current Protocols in Protein Science (CPPS) (John E. Coligan, et. al., ed., John Wiley and Sons, Inc.) and Current Protocols in Immunology (CPI) (John E. Coligan, et. al., ed. John Wiley and Sons, Inc.), which are all incorporated by reference herein in their entireties.

It is understood that the following detailed description and the following examples are illustrative only and are not to be taken as limitations upon the scope of the invention. Various changes and modifications to the disclosed embodiments, which will be apparent to those of skill in the art, may be made without departing from the spirit and scope of the present invention. Further, all patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and do not constitute any admission as to the correctness of the dates or contents of these documents.

BRIEF DESCRIPTION OF THE DRAWINGS

FIGS. 3A-3D demonstrate the relationship between the suppression efficiency of the methods described herein and "primer distance" and PCR extension times. FIGS. 3A-3B depict schematics of an exemplary experiment. As used herein, "primer distance" is defined as the distance between the 5'-end of the forward selective primer and 3'-end of the reverse primer when both are hybridized to the complementary extension sequence of a suppression target sequence. The suppression efficiency is measured by number of cycles deterred (delta Ct) with respect to PCR amplification using exactly same primer set except without the 5' suppression sequence or tail portion of a forward selective primer (standard primer set) in real time PCR or quantitative PCR experiments. In a PCR of perfect amplification efficiency (efficiency of 1), 10 cycle delta Ct corresponds to about 1000 (~$2^{10}$) fold suppression. FIG. 3C shows the delta Ct or equivalent cycles of suppression between qPCR from the standard and forward selective primers plotted against the primer distance. Different lines correspond to different extension times. This figure demonstrates that suppression efficiency drops at short primer distance (10-200 bp), except close to 0 bp. FIG. 3D shows the delta Ct or equivalent cycles of suppression between qPCR from the standard and forward selective primers plotted against extension time This figure demonstrates there is an optimum extension time (around 15 sec for this exemplary polymerase used) for suppression.

FIG. 4 demonstrates the relationship between suppression efficiency of the methods described herein and loop sequence sizes or spacer sequences between the 5' suppression sequence and the 3'end target-specific priming sequence of the forward selective primer. Loop size (delta) is defined as distance (in bp) between 3'-end of the 5' suppression sequence and the 5'-end of the 3' priming sequence of the forward selective primer. The figure demonstrates that the smaller the loop size, the better the suppression in the short primer distance region (50~200 bp). This suggests, without wishing to be bound or limited by theory, that the drop in suppression efficiency in short primer distances are used is due to the balance between stem loop formation speed and polymerase synthesis speed.

FIG. 13 depicts an embodiment of the methods described herein that requires: (i) a 5' suppression sequence or tail sequence, at the 5' end of a forward selective primer, designed to be substantially identical to the suppression target sequence(s) for which amplification is to be suppressed and (ii) the use of a 5' to 3' exonuclease minus polymerase. The forward selective primer, also termed a Nunchaku primer, first anneals to the amplification target sequence and at least one target suppression sequence and gets extended to form a first synthesized strand termed the complementary extension sequence. After denaturation, during the subsequent annealing and extension phases, the sequence complementary to the suppression target sequence of the complementary extension sequence hybridizes to its complementary sequence in the 5' tail and forms a loop. The extended complementary sequence generated from the amplification target sequence does not form this loop. When the polymerase extends from the reverse primer bound to the complementary sequence, it is blocked at the loop for the complementary extension sequence generated from the suppression target sequence(s), but is not blocked for the complementary extension sequence generated from the amplification target sequence.

FIG. 14 demonstrates superior suppression mediated by an embodiment of the tail-loop suppression PCR methods described herein over PCR clamping and restriction-enzyme based suppression methods. PCR clamping is currently considered a representative method for suppression PCR. It uses a $3^{rd}$ oligonucleotide in addition to two standard PCR primers, and this $3^{rd}$ clamping oligonucleotide needs to be modified at its 3' end to inhibit polymerase extension. Heat stable restriction enzyme can be used to break the dominant nucleic acid sequence in the area of sequence difference between one or more variants. The use of restriction enzymes is inconvenient and limited as there must be a restriction enzyme site recognized by a heat-stable restriction enzyme present at the sequence of interest that can discriminate between the sequences, which is a criterion difficult to meet in most cases. Suppression capability was measured as the difference in cycle number in real time PCR, as demonstrated herein. Whether compared to PCR clamping or to restriction enzyme based suppression methods, the tail-loop PCR methods described herein had greatly increased suppression capability—approximately $2^9$ times better than the restriction enzyme technique (~500×) and $2^{13}$ times better than the PCR clamp technique (~8000×).

DETAILED DESCRIPTION

Figure 1:
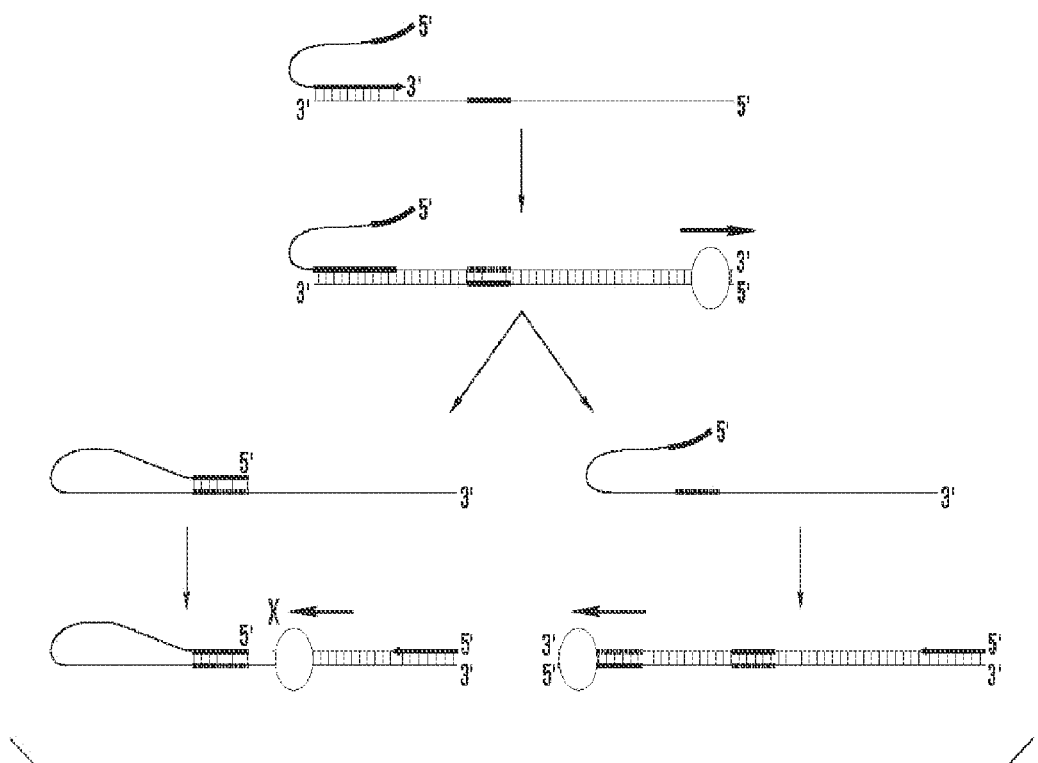
FIG. 1 depicts a schematic of an embodiment of the tail-loop suppression PCR methods described herein. First, a Nunchaku Primer (NP), also referred to herein as a forward selective primer, binds to or hybridizes to its target sequences and extends. After a denaturing step and subsequent annealing and extension steps, the 5' suppression sequence of the forward selective primer hybridizes to a portion of the complementary sequence of the suppression target sequence (or non-target nucleic acid sequence) (left side), forming a stem loop, and preventing a modified polymerase without 5'-3' exonuclease activity from synthesizing the complementary strand of the complementary extension sequence to completion, thus failing to generate sequences with binding sites for both the forward selective primer and the reverse primer in subsequent rounds of amplification. Thus, the amplification product derived from the suppression target sequence or non-target sequence only amplifies cubically or quadratically, i.e., is suppressed relative to sequences that amplify exponentially. On the other hand, target amplicons or amplification target sequence amplicons, which do not comprise the sequence to which the 5' suppression sequence hybridizes, do not have interference in the polymerase extension step, and thus these amplification target sequence amplicons can amplify exponentially.

Described herein are novel approaches for the detection, identification, and/or selective amplification of specific species or variants of nucleic acid sequences within excess of unwanted similar sequences or variants, which are actively suppressed. Accordingly, the approaches described herein provide methods, assays, and kits for selectively amplifying and/or quantifying a target nucleic acid variant present in, or isolated from, a sample of interest, despite the presence of similar, sequence-related non-target nucleic acid variants, such as for example, a rare variant, using primers termed "nunchaku primers" or "forward selective primers."

The novel methods, assays, and kits for suppression PCR described herein provide improved suppression efficiency, broader design options, and reduced costs. The methods, assays, and kits provided herein comprise: a) using a template-dependent DNA polymerase that lacks 5'-3' exonuclease activity, and b) using a PCR primer, termed herein as a "forward selective primer" or a "nunchaku primer" that is generally about 20-40 base pairs longer than a normal primer. Therefore, the costs of the assays described herein are almost equivalent to that of a standard PCR assay. Moreover, as demonstrated herein, design of the forward selective primer is easy and robust, unlike other suppression PCR methods in which, for example, the melting temperatures of the primers have to be carefully adjusted.

Suppression is achieved during the extension phase of a PCR cycle, using the methods of tail-loop suppression PCR described herein. A forward selective primer is deigned and selected so that it comprises a sequence, the "3' priming sequence," that hybridizes to the target nucleic acid sequence to be amplified, termed the amplification target sequence, and to at least one non-target nucleic acid sequence to be suppressed, termed the suppression target sequence. Polymerase extension of the hybridized forward selective primer results in an extension product referred to herein as the "complementary extension sequence," which comprises, in the 5' to 3' direction, the forward selective primer sequence and a sequence complementary to the amplification target sequence or a sequence complementary to the at least one suppression target sequence. Upon subsequent denaturation and annealing steps, the "5' end suppression sequence," which is designed to loop back on and hybridize to a sequence within the complementary extension sequence of the suppression target sequence that is unique to the suppression target sequence, and 3' of the forward selective primer sequence, blocks extension (by DNA polymerase lacking 5' to 3' exonuclease activity) of the complementary strand from the reverse primer (see, for example, FIGS. 1 and 13). As described herein, we have found that these methods of tail-loop suppression PCR can be used to detect differences down to a single base pair. In some embodiments, such as when detecting small deletions, the methods, assays, and kits described herein can easily be used to overcome million-fold or more excesses of sequences not desired to be amplified, as demonstrated herein.

Thus, the novel tail-loop suppression PCR methods, assays, and kits described herein, that utilize forward selective primers and template-specific DNA polymerases that lack 5'-3' exonuclease activity: are robust and do not require restriction enzymes, additional primers, or specific modified nucleotides; can detect differences down to single base pair differences; and can easily be used to overcome million-fold or more excesses of even closely related sequences not desired to be amplified, as demonstrated herein.

The suppression PCR methods, assays, and kits described herein are useful for a variety of applications, such as, for instance, for distinguishing rare variants or mutations, and/or identifying and selectively amplifying specific members of gene families. For example, for many cancers, tumor DNA, either free or in cells, can is found in a patient's blood, but detection of the cancer DNA is difficult because cancer DNA can be highly similar to normal DNA sequences, and only differ at specific, limited de novo mutation sites, or through epigenetic changes. Accordingly, using the tail-loop suppression PCR methods, assays, and kits described herein, if these sequence differences are known, they can be detected at even trace levels if amplification of the normal sequences in non-tumor cells can be suppressed. For example, nucleic acid sequences containing mutations within a short sequence region in a tumor cell can be amplified using the methods described herein, while amplification of a more common wild-type sequence variant, as occurs, for example, in normal, non-tumor cells, is suppressed. The suppression PCR approaches described herein can also be used to monitor the recurrence of a tumor. In such embodiments, a sequence difference identified in a patient's tumor cell is exploited to design a personalized forward selective primer with a 5' suppression sequence targeting the wild-type sequence and permitting efficient amplification only of the patient's tumor variant sequence. Periodic monitoring of blood or other tissue samples can identify a tumor recurrence at an early stage.

The tail-loop suppression PCR methods, assays, and kits described herein can also be applied to the selective amplification of nucleic acids of a minor species (e.g., of a bacterial species or a viral strain) in an environment, by suppression of amplification of sequences of the dominant species or strain. The tail-loop suppression PCR methods, assays, and kits described herein can also be applied to detection or identification of contaminations or infections in the food and agriculture industries. For example, the tail-loop suppression PCR methods, assays, and kits described herein can be used to detect the presence of genetically modified organisms or plants. The suppression PCR methods, assays, and kits described herein are also applicable to the selective amplification of nucleic acid sequences for research applications, such as screening for deletions in model animals, such as C. elegans, as but one example. The tail-loop suppression PCR methods, assays, and kits described herein are also useful for suppression of dimer amplification during nucleic-acid based library constructions. Accordingly, the methods, assays, and kits described herein are useful for a wide variety of applications, including, for example, cancer screening assays and kits, personalized screening assays, SNP (single nucleotide polymorphism) genotyping and identification, and downstream applications such as next generation high-throughput genomic sequencing and library construction.

The terms "suppression polymerase chain reaction" or "suppression PCR" refer to amplification methods in which amplification of one or more sequences or variants, present in much larger quantities in a sample, relative to a desired, closely related sequence, is selectively suppressed to permit detection of a specific, target nucleic acid variant to be amplified, for example, a rare variant, even in the presence of an excess of wild-type or variant sequence. The methods described herein are also referred to as "tail-loop suppression PCR."

Other exemplary methods of suppression PCR exist, but are hampered by various constraints, including the need to use particular modified nucleic acids, and/or the need for additional primers, as well as not being particularly robust or having limited applications. For example, the "PCR clamp" suppression PCR method uses, in addition to two primer oligonucleotides, a third oligonucleotide that is modified at its 3'-end to block polymerase extension. When performing PCR Clamp methods of suppression PCR, it is often times necessary to use peptide nucleic acids (PNA) or locked nucleic acids (LNA) to obtain reasonable suppression efficiency. Other suppression PCR methods require the use of restriction enzymes. For example, restriction enzyme-based suppression PCR methods require a restriction site that exists in the sequence to be suppressed and not in the sequence desired to be amplified, which imposes inflexibility in the assay design. When higher suppression is desired using such methods, restriction enzymes with full activity level at a range of temperatures, such as 60-90° C., e.g., PspGI, are required, which further imposes restrictions in assay design. "Pan-handle suppression" PCR methods use a single primer to generate amplification products or amplicons. Using pan-handle suppression methods, when amplicon sizes are small, single-stranded amplicons generated after denaturation phase form a hairpin (pan-handle) structure in the synthesized strand because of complementary primer sequences at both ends. This hairpin structure in subsequent steps prevents a free primer from binding and further creating a new strand. This form of suppression PCR is almost exclusively used in library construction applications where suppression of homo-adapter dimer or homo-adapter ligates (i.e., same type of adapter ligated to both ends of an insert target sequence, in contrast to hetero-adapter ligates) is desired. However, the requirements for the suppression (complementary sequences at both ends and small amplicon size) make this method difficult to perform. "Headloop suppression" methods described in the art utilize Taq polymerase that has 5'-3' exonuclease activity. After the second round of complementary strand synthesis, a 3'-head synthesized from a primer comprising a 5'-head hybridizes to a complementary sequence forming a loop and acting as a primer. That is, in headloop suppression, the hybridized stem-loop provides a 3' end that is a substrate for extension by polymerase, rather than a 5' end that blocks primer extension. When extension from this headloop primer is complete, the product forms a big hairpin, thus invoking pan-handle type suppression.

Accordingly, provided herein, in some aspects, are methods for detecting the presence of one of two or more variants of a nucleic acid sequence in a nucleic acid sample, the methods comprising:

(a) hybridizing a forward selective primer to a nucleic acid sample comprising an amplification target sequence and a suppression target sequence, wherein the forward selective primer comprises: (i) a 3' end priming sequence that is fully complementary and hybridizes to a portion of the amplification target sequence and the suppression target sequence, and (ii) a 5' end suppression sequence that is substantially identical to a portion of the suppression target sequence, wherein the portion of the suppression target to which the 5' suppression sequence is substantially identical is 5' of the portion of the suppression target sequence to which the 3' end priming sequence hybridizes;

(b) extending the hybridized forward selective primer of step (a) using a polymerase enzyme, the extension generating hybridized duplexes comprising: (i) the amplification target sequence and a hybridized complementary extension sequence, wherein the complementary extension sequence comprises, in the 5' to 3' direction, the forward selective primer and a sequence complementary to the amplification target sequence, and (ii) the suppression target sequence and a hybridized complementary extension sequence, wherein the complementary extension sequence comprises, in the 5' to 3' direction, the forward selective primer and a sequence complementary to the suppression target sequence;

(c) denaturing the hybridized duplexes of step (b) to separate target sequences and complementary extension sequences; and (d) hybridizing a reverse primer to the complementary extension sequences of step (c), and extending the hybridized reverse primer using a 5' to 3' polymerase that lacks 5' to 3' exonuclease activity, wherein if the complementary extension sequence comprises the sequence complementary to the suppression target sequence, then amplification is suppressed and a shorter amplification product is generated, and wherein if the complementary extension sequence comprises the sequence complementary to the amplification target sequence, then amplification is not suppressed and a longer amplification product is generated, whereby the presence of one of two or more variants of a nucleic acid sequence is detected.

The components and steps of the various aspects and embodiments of the methods, assays, and kits described herein are provided in more detail below Nucleic Acid Samples A nucleic acid sample for use with the various aspects and embodiments of the methods, assays, and kits described herein comprises or is presumed to comprise, contain, or be comprised by a target nucleic acid sequence variant of interest desired to be amplified, i.e., a specific species of a nucleic acid sequence, such as a rare allelic variant or mutant, for example. A nucleic acid sample comprises nucleic acids that can serve as templates for and/or substrates for use with any of the methods, assays, or kits described herein. Accordingly, the terms "sample" or "nucleic acid sample" refer to any substance comprising or presumed to comprise a nucleic acid, and includes, for example, a cellular extract, a tissue extract, or fluid extract, isolated from an individual(s) or organism, or any polynucleotide(s) purified or isolated from such materials, such as cellular, tissue or fluid extracts, including, but not limited to, skin, blood, plasma, serum, saliva, spinal fluid, lymph fluid, synovial fluid, bronchial lavage fluid, gut lavage fluid, urine, tears, feces, cells, organs, tumors, and also to samples of in vitro cell culture constituents (including, but not limited to, conditioned medium resulting from the growth of cells (including prokaryotic and eukaryotic cells) in cell culture medium, recombinant cells, and cell components). Nucleic acid samples obtained from environmental sources are also included among "samples" to which the methods described herein can be applied.

In most instances, the nucleic acid molecules from a given nucleic acid sample source are isolated or purified to some degree to provide nucleic acid molecules in a form accessible to or suitable for performing or using with the methods, assays, and kits described herein. Typically, such isolation methods include purification of nucleic acid molecules by standard methods known to one of skill in the art, such as cell lysis, phenol/chloroform extraction, electrophoresis, and/or chromatography. Often, such isolation methods can include a step where nucleic acid molecules are precipitated, e.g., with ethanol, and resuspended in an appropriate buffer for subsequent PCR reactions using the methods as described herein.

The steps of isolating a nucleic acid sample for use with the methods, assays, and kits described herein can, in some embodiments, further comprise one or more additional steps to further purify the nucleic acid sample. For example, step(s) to isolate or purify substantially only DNA molecules, but substantially no RNA molecules or vice versa. In other embodiments, the one or more additional steps to further purify the nucleic acid sample can be used to isolate or purify a specific subtype of nucleic acid, e.g., substantially only genomic DNA, substantially only mitochondrial DNA, substantially only mRNA, substantially only microRNA, etc. In other embodiments of the methods, assays, and kits described herein, the steps of isolating or preparing a nucleic acid sample do not comprise any step of isolating a specific type of nucleic acid, e.g., DNA or RNA. In other words, in some embodiments, the isolation steps do not distinguish between different types or classes of nucleic acids, such that the nucleic acids used in subsequent steps comprise most, if not all, the types and/or subclasses of nucleic acids found in the original sample.

Following such isolation and/or purification steps, in some embodiments of the methods, assays, and kits described herein where one or more nucleic sequences in a sample comprises an RNA sequence, an isolated/purified sample can first be reverse transcribed into one or more cDNAs. For example, if the suppression PCR methods described herein are used to selectively amplify an isoform of a gene that has low expression relative to a dominant isoform and suppression of the dominant isoform is desired for detection. In such embodiments, following the reverse transcription steps, a sample can be further treated to remove any starting RNA template sequences, using any suitable method, including physical, chemical, or enzymatic means, which are known to those of skill in the art, to separate hybridized nucleic acid strands. A physical approach for strand separation involves heating the nucleic acid until it is completely (>99%) denatured, which typically involves temperatures ranging from about 80° C. to about 105° C., for times ranging from a few seconds to minutes. Such denaturing methods can also be used to kill or terminate any reverse transcriptase activity present in the sample. In other embodiments, RNA-specific degrading enzymes can be used to degrade any RNA remaining following cDNA transcription, such as RNase H.

Amplification Target and Suppression Target Nucleic Acid Sequences

The tail-loop suppression PCR methods, assays, and kits described herein are particularly suited for the selective amplification of a target nucleic acid, termed the "amplification target sequence," and active suppression of at least one non-target nucleic acid sequence to be suppressed, termed the "suppression target nucleic acid," in a sample comprising multiple, closely related sequences. In particular, the methods, assays, and kits allow amplification and detection of a rare variant present in a mixture or sample comprising much larger quantities of other closely related sequence variants. The terms "amplification target sequence," "amplification target nucleic acid," "amplification target nucleic acid sequence," "amplification target nucleic acid variant," "amplification target oligonucleotide," and "amplification target polynucleotide," as used in regard to the various aspects and embodiments of the methods, assays, and kits described herein, refer to a nucleic acid of interest, e.g., a nucleic acid of a particular nucleotide sequence, one wishes to selectively detect and/or quantify in a sample via amplification using the tail-loop suppression PCR methods and assays described herein. The term can refer to a single-stranded or double-stranded polynucleotide molecule (e.g., RNA, DNA, or a combination thereof), or a specific strand thereof, to which, for example, an oligonucleotide primer, such as a forward selective primer or forward suppression primer, that is "specific for" the target nucleic acid anneals or hybridizes. An amplification target sequence, as used herein, comprises a forward selective primer binding sequence, but does not comprise a sequence that is substantially identical to the 5' end suppression sequence of a forward selective primer, as these terms are used herein.

As used in regard to the various aspects and embodiments of the methods, assays, and kits described herein, the terms "suppression target sequence," "suppression target nucleic acid," "suppression target nucleic acid sequence," "suppression target nucleic acid variant," "suppression target oligonucleotide," and "suppression target polynucleotide," refer to nucleic acid sequences one does not wish to selectively detect and/or amplify and/or quantify in a sample, but instead wishes to actively suppress the amplification of by use of a forward selective primer in the tail-loop suppression PCR methods, assays, and kits described herein. In other words, a suppression target sequence refers to any sequence of which the amplification is actively suppressed using the forward selective primers in the methods, assays, and kits described herein. Typically, the suppression target sequence (s) are in large excess of quantity over the amplification target sequence, and have closely related sequences to the amplification target sequence. A suppression target sequence to be suppressed using the tail-loop suppression PCR methods, assays, and kits described herein comprises both a sequence that is substantially identical to the 5' end suppression sequence of a forward selective primer, as well as a forward selective primer binding sequence.

Accordingly, in some embodiments of the methods, assays, and kits described herein, a nucleic acid sample comprises one or more related variant nucleic acid sequences, such that using a forward selective primer permits selective amplification of one of the variant sequences, which acts as the amplification target sequence, with suppression of at least one of the other variant sequences or suppression target sequences.

Two nucleic acid sequences are said to be variants of each other if they comprise identical sequences for most, for example, 90% of the entire length of a sequence to be amplified using the tail-loop suppression PCR methods, assays, and kits described herein, but have one or more nucleotide differences (polymorphisms), deletions, or additions/insertions. In other words, for the purposes of use with the methods, assays, and kits described herein, two nucleic acid sequences are said to be variants of each other when they comprise sequences that are at least 90% identical, at least 91% identical, at least 92% identical, at least 93% identical, 94% identical, at least 95% identical, at least 95% identical, at least 96% identical, 97% identical, at least 98% identical, at least 99% identical, or more identical, but not 100% identical, over the length of the nucleic acid sequence to be amplified using the methods described herein.

In regard to the various aspects and embodiments of the methods, assays, and kits described herein, the terms "nucleic acid," "polynucleotide," and "oligonucleotide" generally refer to polyribonucleotide or poly-deoxyribonucleotide, and includes unmodified RNA, unmodified DNA, modified RNA, and modified DNA. Polynucleotides include, without limitation, single- and double-stranded DNA and RNA polynucleotides. Accordingly, the term polynucleotide, as it is used herein, includes chemically, enzymatically or metabolically modified forms of polynucleotide sequences, as well as the naturally occurring chemical forms of DNA and RNA found in or characteristic of viruses and cells, including for example, simple (prokaryotic, bacterial) and complex (eukaryotic) cells. A nucleic acid polynucleotide or oligonucleotide for use in or with the methods, assays, and kits described herein retains the ability to hybridize to its cognate complimentary strand.

In regard to the various aspects and embodiments of the methods, assays, and kits described herein, the terms "nucleotide" or "mononucleotide" refer to a phosphate ester of a nucleoside, e.g., mono-, di-, tri-, and tetraphosphate esters, where the most common site of esterification is the hydroxyl group attached to the C-5 position of the pentose (or equivalent position of a non-pentose "sugar moiety"). The term "nucleotide" includes both conventional nucleotides, as well as non-conventional nucleotides which include, but are not limited to, phosphorothioate, phosphite, ring atom modified derivatives, and the like.

Because mononucleotides are reacted to make poly- and oligonucleotides in a manner such that the 5' phosphate of one mononucleotide pentose ring is attached to the 3' oxygen of its neighbor in one direction via a phosphodiester linkage, an end of an oligonucleotide is referred to as the "5' end" if its 5' phosphate is not linked to the 3' oxygen of a mononucleotide pentose ring, and as the "3' end" if its 3' oxygen is not linked to a 5' phosphate of a subsequent mononucleotide pentose ring. As used in regard to the various aspects and embodiments of the methods described herein, a nucleic acid sequence, even if internal to a larger oligonucleotide, also can be said to have 5' and 3' ends. For example, an amplification target sequence to be amplified using the methods described herein within a larger nucleic sequence can be said to have a 5' and 3' end.

Primers and Forward Selective Primers

Oligonucleotide primers used in PCR methods act as a point of initiation or priming for the synthesis and extension of a strand complementary to a sequence of a nucleic acid to which they hybridize, when placed under conditions in which primer extension can be catalyzed. Accordingly, an "oligonucleotide primer," as used in regard to the various aspects and embodiments of the methods, assays, and kits described herein, refers to any polynucleotide molecule (i.e., DNA, RNA, a molecule comprising artificial nucleotides, or any combination thereof) capable of annealing or hybridizing to a portion of a sequence of a target nucleic acid and providing a 3' end substrate for a polymerase enzyme to produce an enzymatic extension product that is complementary to the nucleic acid to which the polynucleotide is annealed. In some preferred embodiments of the methods described herein, an oligonucleotide primer is not an RNA molecule, or does not comprise ribonucleotides. A primer as described herein can be provided as a single- or double-stranded molecule. That is, in some embodiments of the methods described herein, a primer is not double-stranded. A primer is preferably single-stranded for maximum efficiency in amplification. The conditions for initiation and extension from a primer hybridized or annealed to a nucleic acid sequence usually include the presence of four different deoxyribonucleoside triphosphates (dNTPs) and a polymerization-inducing agent, such as a DNA polymerase or a reverse transcriptase, in a suitable buffer ("buffer" includes constituents that are cofactors for the enzymatic reactions, and/or which affect pH, ionic strength, etc.) and at a suitable temperature.

Primers for use in PCR methods, such as the tail-loop suppression PCR methods, assays, and kits described herein, unless otherwise specified (as for example, with forward selective primers, which can have additional design considerations as discussed herein) are generally less than or equal to 150 nucleotides in length, e.g., less than or equal to 140 nucleotides in length, less than or equal to 130 nucleotides in length, less than or equal to 120 nucleotides in length, less than or equal to 110 nucleotides in length, less than or equal to 100 nucleotides in length, less than or equal to 90 nucleotides in length, less than or equal to 80 nucleotides in length, less than or equal to 70 nucleotides in length, less than or equal to 60 nucleotides in length, less than or equal to 50 nucleotides in length, less than or equal to 40 nucleotides in length, less than or equal to 30 nucleotides in length, less than or equal to 20 nucleotides in length, or less than or equal to 15 nucleotides in length, but preferably at least 10 nucleotides in length. Primers, such as reverse primers, for use with the tail-loop suppression PCR methods, assays, and kits described herein can be of a variety of lengths and are preferably less than 50 nucleotides in length and greater than 6 nucleotides in length, preferably 6-35 nucleotides, more preferably 12-30 nucleotides, and most preferably 15-25 nucleotides in length. Accordingly, oligonucleotide primers or priming sequences are usually at least 6 bases, at least 8 bases, at least 10 bases, at least 12 bases, more often about 15 bases, about 16 bases, about 17 bases, about 18 bases, about 19 bases, about 20 bases, about 21 bases, about 22 bases, about 23 bases, about 24 bases, or about 25 bases in length, unless otherwise specified, as with forward selective primers, which have additional design considerations, as explained herein.

A key and distinguishing feature of the methods, assays, and kits provided herein for suppression PCR is the use of an oligonucleotide primer, termed a "forward selective primer" or "nunchaku primer," that is designed to selectively amplify an amplification target nucleic acid sequence and actively suppress amplification of at least one suppression target nucleic acid sequences. It is noted that any PCR primer can be considered "selective" in that it normally permits template-dependent extension only when hybridized to a complementary sequence. However, as used herein, and in contrast to a standard PCR primer which substantially has only priming activity, a selective primer, e.g., a "forward selective primer" or "reverse selective primer" has both priming activity and suppression activity. That is, a "selective primer" as the term is used herein, has 3' terminal sequence that primes sequence- and template-dependent synthesis and 5' terminal sequence that substantially inhibits or blocks the advance of a polymerase when hybridized in the way of an advancing polymerase generating the opposite strand.

As noted, the selective primers used herein are also referred to as "nunchaku primers," in analogy to their similarity to the weapon of that name when drawn schematically (see, e.g., FIG. 1). While the description herein most often refers to "forward selective primers," this is done for clarity and for illustration and does not imply that the opposite strand or "reverse" primer cannot be a nunchaku-type primer as well. Thus, in one embodiment of the methods, assays and kits described herein, both the forward and reverse primers are nunchaku-type or selective primers as that term is defined above. In the embodiments in which both the forward and reverse primer are selective primers of this kind, the suppression sequence (or its complement, as the case may be) can be the same, i.e., both primers hybridize to the same suppression sequence/suppression sequence complement. Alternatively, the forward and reverse selective primers can target different sequences for suppression. This can increase suppression efficiency and/or suppress a separate type of variant—this is discussed further herein in terms of embodiments applicable, for example, to library construction, in which suppression targets include primer dimers and carrier sequences to which primers have become ligated.

As described herein, through the use of these forward selective primers, nucleic acid sequences that are highly similar to each other can be distinguished, and selective amplification of an amplification target nucleic acid sequence and suppression of a suppression target nucleic acid sequence can be achieved, using a single pair of primers, i.e., the forward selective primer and a common reverse primer. The forward selective primer is designed to comprise both a priming sequence that binds to both the amplification target nucleic acid sequence and the suppression target nucleic acid sequence, and thus acts as a common priming sequence, as well as a "5' suppression sequence" that is identical to a portion of the suppression target nucleic acid sequence(s) but not to the amplification target nucleic acid sequence, thereby permitting selective suppression of the suppression target nucleic acid sequence(s) during subsequent PCR cycles, as explained in more detail herein.

Accordingly, as used in regard to the various aspects and embodiments of the methods, assays, and kits for tail-loop suppression PCR described herein, the terms "forward selective primer" or "nunchaku primer," refer to a primer comprising (i) a 3' end priming sequence that is complementary to and can hybridize to both an amplification target nucleic acid sequence and a suppression target nucleic acid sequence, and provide a 3' end substrate for a polymerase enzyme, and (ii) a 5' end suppression sequence or 5' tail sequence that is substantially identical to a portion of the suppression target nucleic acid sequence(s) but not to a portion of the amplification target nucleic acid sequence in a nucleic sample.

The 3' end priming sequence of a forward selective primer is designed so that it is complementary to and binds or hybridizes to a sequence that is common to or shared by the amplification target nucleic acid sequence and a suppression target nucleic acid sequence (such as, for example, a wild-type variant of the amplification target sequence), and is of sufficient length to anneal under PCR annealing conditions and provide a 3' end substrate for a polymerase enzyme. This shared primer binding sequence to which the forward selective primer is complementary and hybridizes to is termed herein the "forward selective primer binding site." In other words, the 3' end priming sequence is designed to hybridize to the forward selective primer binding site on both the amplification target nucleic acid sequence and the suppression target nucleic acid sequence for extension by a 5' to 3' polymerase under PCR annealing conditions. In general, the terms "primer site" or "primer binding site" refers to the segment of the sequence of a nucleic acid sequence to which a primer hybridizes, i.e., the primer is specific for or complementary to the primer binding site. It is preferred, in some embodiments, that a primer, such as a forward selective primer, anneals or hybridizes to its primer binding site under stringent conditions. By "stringent conditions" is meant that the conditions under which hybridization or annealing is occurring permit only hybridization between nucleic acid sequences that are highly complementary, e.g., only a forward selective primer "specific for" the amplification target nucleic acid sequence and the suppression target nucleic acid sequence(s) will hybridize under stringent conditions. Stringency can be increased, for example, by increasing the temperature of and/or decreasing the salt concentrations in a reaction mixture.

Binding of the 3'end priming sequence to the forward selective primer binding site on the amplification target nucleic acid sequence or the suppression target nucleic acid sequence, upon extension by a 5' to 3' polymerase, results in a "complementary forward selective primer extension sequence" or "complementary extension sequence." Accordingly, as used herein, the complementary extension sequence comprises, in the 5' to 3' direction, the forward selective primer sequence and a sequence complementary to the amplification target nucleic acid sequence, or the forward selective primer sequence and a sequence complementary to the suppression target nucleic acid sequence.

The 5' end suppression sequence of a forward selective primer is designed to suppress amplification of any complementary extension sequences comprising a sequence complementary to a suppression target nucleic acid sequence(s). Accordingly, the 5' end suppression sequence is designed to hybridize to a portion of the complementary extension sequence that comprises the sequence complementary to the suppression target nucleic acid sequence, and therefore prevent extension from a reverse primer by a 5' to 3' polymerase enzyme lacking 5' to 3' exonuclease activity. The portion of the suppression target nucleic acid extension sequence(s) to which the 5' end suppression sequence binds is 3' of (or "downstream" of) the 3' end of the forward selective primer sequence of the complementary extension product. Based on this complementarity, the 5' end suppression sequence is substantially identical to a portion of the suppression target nucleic acid sequence(s) that is 5' or proximal of the forward selective primer binding site of the suppression target nucleic acid sequence. In some embodiments, the suppression target nucleic acid sequence can be selected such that 2 or more, or even all, variants of a nucleic acid sequence are suppressed except for the variant corresponding to the amplification target sequence.

Accordingly, a forward selective primer, as used in the various aspects and embodiments of the methods, assays, and kits described herein is generally at least 30 nucleotides in length, e.g., at least 40 nucleotides in length, at least 50 nucleotides in length, at least 60 nucleotides in length, at least 70 nucleotides in length, at least 80 nucleotides in length, at least 90 nucleotides in length, at least 100 nucleotides in length, at least 110 nucleotides in length, at least 120 nucleotides in length, at least 130 nucleotides in length, at least 140 nucleotides in length, at least 150 nucleotides in length, or more.

It is preferred that the 3' end priming sequence is generally at least 6 nucleotides in length, at least 8 nucleotides in length, at least 10 nucleotides in length, at least 12 nucleotides in length, more often about 8-30 nucleotides in length, e.g., 10-25 nucleotides in length, 10-20 nucleotides in length, 8-15 nucleotides in length, 15-30 nucleotides in length, 15-25 nucleotides in length, or 15-20 nucleotides in length.

It is also preferred that the 5' suppression sequence of the forward selective primer is generally at least 5-10 nucleotides in length, e.g., at least 10 nucleotides in length, at least 15 nucleotides in length, at least 20 nucleotides in length, at least 30 nucleotides in length, at least 35 nucleotides in length, at least 40 nucleotides in length, at least 45 nucleotides in length, at least 50 nucleotides in length, at least 55 nucleotides in length, at least 60 nucleotides in length, at least 65 nucleotides in length, at least 70 nucleotides in length, at least 75 nucleotides in length, or more, in length. The length and sequences of primers for use in PCR and the methods described herein can be designed, in part, based on principles known to those of skill in the art, see, e.g., Innis M A and Gelfand D H (1990; "Optimization of PCRs." In: PCR protocols. A guide to methods and applications. Academic Press, Inc, Chapter 1:3-12).

The 5' suppression sequence of the forward selective primer is designed to be substantially identical to a portion of the suppression target sequence, and therefore hybridize or bind to the complementary extension sequence of the suppression target sequence to form a stem loop or tail loop that blocks the activity of a polymerase enzyme that lacks 5' to 3' exonuclease activity. As used herein, the term "stem-loop" refers to a nucleic acid secondary structure in which a single strand of nucleic acid, e.g., DNA or RNA, has two self-complementary sequences, separated by some length of intervening sequence, such that the self-complementary sequences can hybridize to form a base paired "stem" connected by a "loop" made up of the non-base paired intervening sequence. The "stem" of a stem-loop will generally be of sufficient length to be stable in a PCR reaction at the extension temperature used for the reaction. As understood by those of skill in the art, the stability of hybridization is affected by the G/C and A/T content of the complementary or, in this case, self-complementary sequences.

The "portion" of the complementary extension sequence to which the 5' end suppression sequence binds to block polymerase activity must be long enough to support stable hybridization of the 5' suppression sequence under the PCR conditions, including temperature conditions, used during an extension cycle. Accordingly, the "portion" of the complementary extension sequence of the suppression target sequence to which the 5' end suppression sequence binds is at least 5-10 nucleotides in length, at least 10 nucleotides in length, at least 11 nucleotides in length, at least 12 nucleotides in length, at least 13 nucleotides in length, at least 14 nucleotides in length, at least 15 nucleotides in length, at least 16 nucleotides in length, at least 17 nucleotides in length, at least 18 nucleotides in length, at least 19 nucleotides in length, at least 20 nucleotides in length, at least 21 nucleotides in length, at least 22 nucleotides in length, at least 23 nucleotides in length, at least 24 nucleotides in length, at least 25 nucleotides in length, at least 30 nucleotides in length, at least 35 nucleotides in length, at least 40 nucleotides in length, at least 45 nucleotides in length, at least 50 nucleotides in length, or more.

As used in regard to the various aspects and embodiments of the methods, assays, and kits described herein, "complementary" refers to the ability of a single strand of a polynucleotide or portion thereof, such as a 3' end priming sequence of a forward selective primer, to hybridize to an anti-parallel polynucleotide strand, or portion thereof, by contiguous base-pairing, i.e., hydrogen bonding, between the nucleotides of the anti-parallel polynucleotide single strand, thereby forming a double-stranded polynucleotide or duplex comprising the complementary strands. A first polynucleotide is said to be "completely complementary" to a second polynucleotide strand if each and every nucleotide of the first polynucleotide forms a hydrogen-bonded base-pair with nucleotides within the complementary region of the second polynucleotide. A first polynucleotide is not completely complementary (i.e., "partially complementary") to the second polynucleotide if at least one nucleotide in the first polynucleotide does not base pair with the corresponding nucleotide within the complementary region of the second polynucleotide, but can still hybridize to the second polynucleotide under some conditions.

The degree of complementarity between polynucleotide sequences has significant effects on the efficiency and strength of annealing or hybridization between polynucleotide strands. This is of particular importance in transcription, extension, and amplification reactions, such as those described in the tail-loop suppression PCR method and assay steps provided herein, which depend upon binding and annealing between different polynucleotide strands. Accordingly, an oligonucleotide primer or portion thereof, such as a 3'end priming sequence of a forward selective primer is "complementary" to a sequence of an amplification target sequence or suppression target sequence(s) if at least 70%, or, more preferably, at least 80%, at least 90%, at least 95%, at least 98%, at least 99%, or more, up to and including 100%) of the nucleotides of the entire primer sequence, or, for example, the entire 3' priming sequence of the forward selective primer, forms hydrogen-bonded base-pairs with nucleotides on the amplification target sequence or suppression target sequence(s). Generally, the 3' terminal nucleotide of a primer must base pair with a corresponding nucleotide on the polynucleotide to which it acts a priming site for a template-dependent polymerase enzyme to extend the primer. It is understood that a forward selective primer, reverse primer, or oligonucleotide molecule that is said to be "specific for" a nucleic acid sequence comprises at least a portion of sequence that is completely complementary to or has a high degree of complementarity to a portion of the sequence of the nucleic acid.

In some embodiments of the methods, assays, and kits described herein, a forward selective primer further comprises a "loop sequence" or "loop spacer sequence" located 5' of the 3' end priming sequence and 3' of the 5' suppression sequence. That is, a "loop sequence" or "loop spacer sequence," if present, is located between the 5' end suppression sequence and the 3' end priming sequence of the forward selective primer. It is preferred that the loop sequence does not comprise a sequence complementary to any portion of the complementary extension sequence. As used herein, the terms a "loop sequence" or a "loop spacer sequence" refer to a heterologous nucleotide sequence in a forward selective primer comprising a known number of nucleotides that does not bind or is not complementary to a complementary extension sequence. The number of nucleotides, or nucleotide analogues thereof, in the loop sequence can range from 2 or more nucleotides, or nucleotide analogues thereof up to and including 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, 21 or more, 22 or more, 23 or more, 24 or more, 25 or more, 30 or more, 35 or more, 40 or more, 45 or more, 50 or more, 55 or more, 60 or more, 65 or more, 70 or more, 75 or more, 80 or more, 85 or more, 90 or more, 95 or more, 100 or more, 105 or more, 110 or more, 115 or more, 120 or more, 125 or more, 130 or more, 135 or more, 140 or more, 145 or more, 150 or more, 155 or more, 160 or more, 165 or more, 170 or more, 175 or more nucleotides or analogues thereof.

Reverse primers used in the suppression PCR methods, assays, and kits described herein are designed to be complementary to or hybridize to a sequence shared by all complementary extension sequences generated by extension of the forward selective primer. In other words, the reverse primer used in the tail-loop suppression PCR methods, assays, and kits described herein is selected or designed to bind to a primer binding site that is shared or identical between a sequence complementary to the amplification target sequence and a sequence complementary to the suppression target sequence(s), according to principles of primer design known to one of ordinary skill in the art and as outlined herein.

The distance between the 5' end suppression sequence of the forward selective primer and the 3'-end of the reverse primer when both are hybridized to the complementary extension sequence of a suppression target sequence, i.e., when the 5' suppression sequence forms a stem loop and binds to a portion of the complementary extension sequence of the suppression target sequence, is termed herein as the "primer distance." As shown at FIGS. 3A-3C, suppression efficiency can vary according to the primer distance. The primer distance for use in the various aspects and embodiments of the methods, assays, and kits described herein can vary according to the length of the suppression target sequence, and other considerations, and can range from 0 nucleotides, up to and including at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 30, at least 35, at least 40, at least 45, at least 50, at least 55, at least 60, at least 65, at least 70, at least 75, at least 80, at least 85, at least 90, at least 100, at least 110, at least 120, at least 130, at least 140, at least 150, at least 160, at least 170, at least 180, at least 190, at least 200, at least 250, at least 300, at least 350, at least 400, or more nucleotides. In some embodiments of the methods, assays, and kits described herein, the primer distance can be a negative primer distance, such that the hairpin loop formed by the 5' suppression sequence bound to a portion of the complementary extension sequence of the suppression target sequence overlaps with the reverse primer binding site. In some such embodiments, the primer distance is at least −1 nucleotide, and can range from at least −2 nucleotides, at least −3 nucleotides, at least −4 nucleotides, at least −5 nucleotides, at least −6 nucleotides, at least −7 nucleotides, at least −8 nucleotides, at least −9 nucleotides, at least −10 nucleotides, or more. For a given method or assay design, specific polymerases, amplification conditions, etc., one skilled in the art can readily evaluate the primer distance effect and choose an appropriate primer arrangement to best exploit suppression as described herein.

Figure 15:
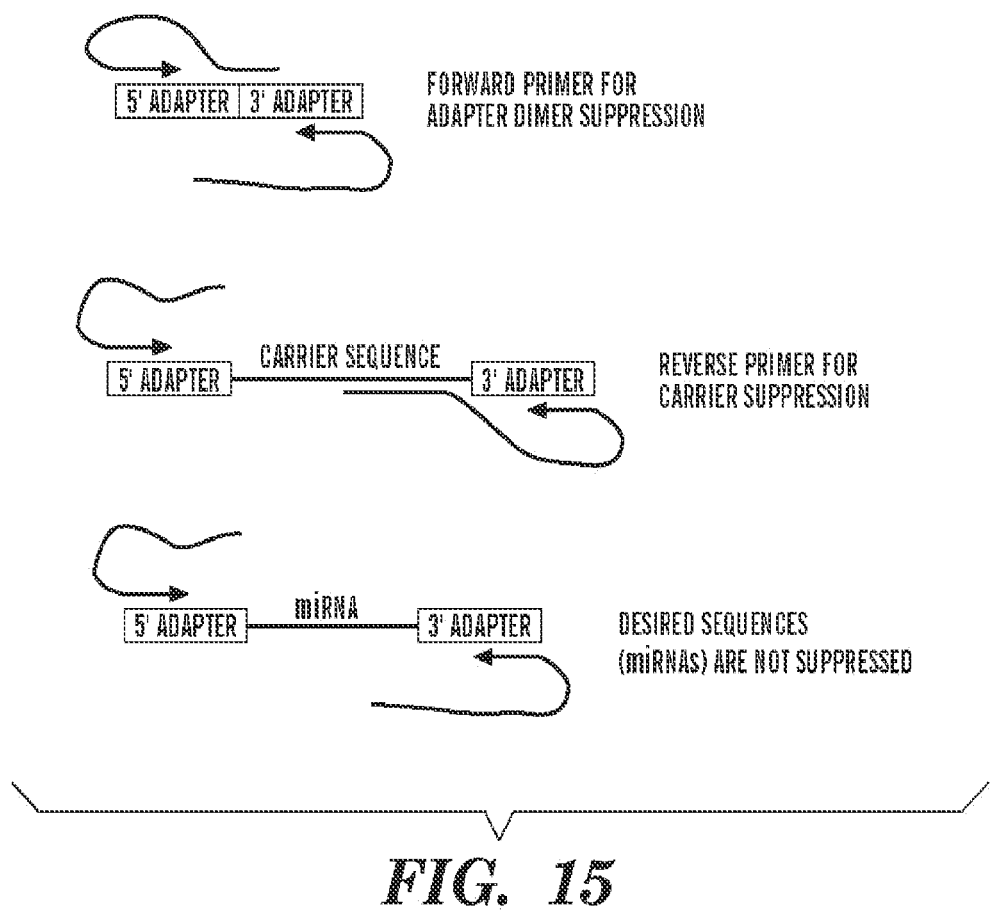
FIG. 15 illustrates application of the tail-loop suppression PCR methods described herein to prevention of amplification of unwanted dimer formation and inserted carrier sequences during the construction of a library of sequences, such as a library of microRNA sequences.

In some embodiments of the methods, assays, and kits described herein, the reverse primer can be designed to also act as nunchaku primer. In such instances, the reverse nunchaku primer or reverse selective primer comprises a 5' suppression sequence that blocks amplification of a different portion of the same suppression target sequence targeted by the forward selective primer (by suppressing in the other direction from forward selective primer), or a sequence comprising an additional second suppression target sequence, for example, a sequence unrelated to the suppression target sequence(s) blocked by the forward selective primer, in a process termed herein as "dual-inhibition." As a non-limiting example, an embodiment using such nunchaku primer pairs is depicted at FIG. 15 in an application of the methods, assays, and kits described herein to prevent amplification of unwanted dimer sequences and inserted carrier sequences. While the 5' suppression sequence of the forward selective primer blocks amplification of dimer formation, by targeting, for example, the unique junction sequence of the dimers, the 5' suppression sequence of the reverse nunchaku primer blocks amplification of inserted carrier sequences. Accordingly, in such embodiments of the methods, assays, and kits described herein, different families or types of variant sequences can be targeted by the forward and reverse primers respectively. In those embodiments of the methods, assays, and kits described herein in which the reverse primer also acts as a nunchaku primer and targets a suppression target sequence different from the forward selective primer, the reverse primer can also be referred to as a "reverse selective primer." Similar to a forward selective primer, a reverse selective primer is designed to comprise (i) a 3' end priming sequence that is complementary to and can hybridize to both an amplification target nucleic acid sequence and a suppression target nucleic acid sequence, and provide a 3' end substrate for a polymerase enzyme, and (ii) a 5' end suppression sequence or 5' tail sequence that is substantially identical to a portion of the suppression target nucleic acid sequence(s) but not to a portion of the amplification target nucleic acid sequence in a nucleic sample.

Oligonucleotide primers, such as forward selective primers and reverse primers, for use in the methods, assays, and kits described herein can be prepared using any suitable method known to those skilled in the art, such as, for example, methods using phosphotriesters and phosphodiesters. In some embodiments, one or more phosphorothioate linkages can be included in the primers. The oligonucleotide primer can also be modified at the base moiety, sugar moiety, or phosphate backbone with minor groove binders, intercalating agents and the like, so long as its ability to specifically bind template and serve as substrate for polymerase extension are maintained.

The primers for use in the methods, assays, and kits described herein can be designed according to known algorithms. Typically, commercially available or custom software use algorithms to design primers such that the annealing temperatures of the primers are close to melting temperature. Primers are typically designed so that all primers participating in a particular reaction have melting temperatures that are within 10° C., preferably within 5° C., and most preferably within 2° C. of each other. Primers are further designed to avoid priming on themselves or another primer as templates in a reaction, and to avoid intra- and intermolecular complementarity. In some embodiments, the oligonucleotide primers for use in the methods described herein have a GC content similar to that of the nucleic acid sequence to which it hybridizes. It is preferred that oligonucleotide primers do not comprise unusual sequence runs, such as stretches of polypurines or polypyrimidines, as such stretches can result in secondary structures that inhibit amplification steps, such as PCR. It is also preferred a given set of oligonucleotide primers, such as a forward selective primer and a reverse primer, do not have complementarity to each other in their 3' ends.

The primers must be of sufficient length and have sufficient complementary to their respective nucleic acid strands to anneal or hybridize selectively and form stable duplexes. In some embodiments of the methods, assays, and kits described herein, oligonucleotide primers or 3' priming sequences within forward selective primers are designed to be exactly complementary to the forward selective primer binding site of the amplification target sequence and suppression target sequence(s). In other embodiments of the methods, assays, and kits described herein, base-pair mismatches or sites of non-complementarity can be included, e.g., to detect gene homologs where sequence information is lacking. In those embodiments where one or more mismatches are to be included in an oligonucleotide primer set, it is preferred that the mismatches or non-complementary sites occur at or closer to the 5' end of the primer, as the closer a mismatch is to the 3' end of a primer, the more likely it is to prevent extension of the annealed primer. As understood by one of skill in the art, when a DNA molecule is said to be "complementary" to an RNA sequence, any C, G, or A nucleotides on the RNA molecule is base-paired with the complementary G, C, and T respectively on the DNA molecule, while any U nucleotides on the RNA molecule are base-paired with A nucleotides on the DNA molecule.

In some embodiments of the methods, assays, and kits described herein, primer concentrations used should be sufficient to bind to the amount of sequences that are amplified so as to provide an accurate assessment of the quantity of amplified sequence. Those of skill in the art will recognize that the amount or concentration of primer should vary according to the binding affinity of the primers as well as the quantity of sequence to be bound. Typical primer concentrations range from, for example, 0.01 µM to 1.0 µM in a reaction.

The terms "hybridizing" or "annealing," as used herein, refer to the hydrogen-bonded base-pairing interaction of one oligonucleotide or polynucleotide with another oligonucleotide or polynucleotide (typically an antiparallel polynucleotide) that results in formation of a duplex of two nucleic acid strands, typically termed a "hybridization complex" or a "hybridized duplex." More specifically, when two sequences are said to "hybridize," as the term is used herein, each sequence is in opposite or reverse orientation with respect to the other sequence, e.g., a 5' to 3' sequence anneals to a complementary sequence that is 3' to 5' with respect to the first sequence. The ability of two oligonucleotide sequences to hybridize is a function of not only the complementarity of the two sequences, but also includes such factors as the temperature under which the two sequences are contacted (higher temperatures inhibit annealing of oligonucleotides), the pH and concentrations and identities of the salt(s) in the reaction mixture, and the concentrations of the respective oligonucleotides. It is not a requirement that two oligonucleotides have 100% complementarity over their full length to achieve hybridization. However, the greater the degree of complementarity, the greater the ability of two sequences to hybridize under what are termed "stringent hybridization conditions," such as those achieved in a typical PCR reaction mixture. Hybridization conditions useful in the methods and assays described herein are well known to those of ordinary skill. Hybridization can be performed at elevated temperatures (such as 40-70° C.) to provide conditions under which only perfectly matched or substantially identical sequences can form a double-stranded complex. Hybridization can be preceded by brief exposure to denaturing temperature conditions (such as heating to 80-90° C.) to relax secondary structures or to separate strands of pre-existing complexes, e.g., during a PCR amplification.

As noted above, an indication that two nucleic acid sequences are highly complementary is that the two molecules hybridize specifically to each other under stringent conditions. The phrase "hybridizing specifically to" refers to the binding, duplexing, or hybridizing of a molecule only to a particular nucleotide sequence under stringent conditions. "Stringent hybridization conditions" in the context of nucleic acid hybridization experiments are sequence dependent, and are different under different environmental parameters. Longer sequences hybridize specifically at higher temperatures. The $T_m$ is the temperature (under defined ionic strength and pH) at which 50% of the strands capable of forming a duplex structure are actually involved in such a structure. For DNA-DNA hybrids, for example, the $T_m$ can be approximated from the equation of Meinkoth and Wahl, *Anal. Biochem.*, 138:267 (1984), which reference is hereby incorporated by reference in its entirety: $T_m$ 81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs $T_m$ is reduced by about 1° C. for each 1% of mismatching; thus, $T_m$ and/or hybridization conditions can be adjusted by one of skill in the art to permit annealing to sequences of the desired complementarity. Generally, stringent conditions are selected to be about 5° C. lower than the thermal melting point ($T_m$) for the specific sequence and its complement at a defined ionic strength and pH. However, highly stringent conditions can utilize a hybridization at 1, 2, 3, or 4° C. lower than the thermal melting point ($T_m$). Using the equation, hybridization, and desired T, those of ordinary skill will understand that variations in the stringency of hybridization are inherently described. An extensive guide to the hybridization of nucleic acids is found in Tijssen, *Laboratory Techniques in Biochemistry and Molecular Biology Hybridization with Nucleic Acid Probes*, Part I Chapter 2 "Overview of Principles of Hybridization and the Strategy of Nucleic Acid Probe Assays," Elsevier, New York (1993), which is hereby incorporated by reference in its entirety.

In some embodiments of the methods, assays, and kits described herein, a primer, such as a forward selective primer or reverse primer comprises conventional nucleotides. As used in regard to the various aspects and embodiments of the methods described herein, the term "conventional nucleotide" refers to one of the "naturally occurring" deoxynucleotides (dNTPs), including dATP, dTTP (or TTP), dCTP, dGTP, dUTP, and dITP. In other words, the term "naturally occurring" refers to a nucleotide that exists in nature without human intervention.

In some embodiments of the methods, assays, and kits described herein, a primer, such as a forward selective primer or a reverse primer comprises one or more non-conventional nucleotides. The term "non-conventional nucleotide," as used in respect to the various aspects and embodiments of the methods, assays, and kits described, refers to any nucleotide that is not a naturally occurring nucleotide. Accordingly, the term "non-conventional nucleotide" refers to a nucleotide that exists only with human intervention, i.e., an "artificial nucleotide." A "non-conventional nucleotide" can include, for example, a nucleotide in which the pentose sugar and/or one or more of the phosphate esters is replaced with a respective analog. Exemplary phosphate ester analogs include, but are not limited to, alkylphosphonates, methylphosphonates, phosphoramidates, phosphotriesters, phosphorothioates, phosphorodithioates, phosphoroselenoates, phosphorodiselenoates, phosphoroanilothioates, phosphoroanilidates, phosphoroamidates, boronophosphates, etc., including any associated counterions, if present. A non-conventional nucleotide can show a preference of base pairing with another non-conventional or "artificial" nucleotide over a conventional nucleotide (e.g., as described in Ohtsuki et al. 2001, Proc. Natl. Acad. Sci., 98: 4922-4925, hereby incorporated by reference). The base pairing ability can be measured, for example, by the T7 transcription assay as described in Ohtsuki et al. Other non-limiting examples of "non-conventional" or "artificial" nucleotides can be found in Lutz et al. (1998) Bioorg. Med. Chem. Lett., 8: 1149-1152); Voegel and Benner (1996) Helv. Chim. Acta 76, 1863-1880; Horlacher et al. (1995) Proc. Natl. Acad. Sci., 92: 6329-6333; Switzer et al. (1993), Biochemistry 32:10489-10496; Tor and Dervan (1993) J. Am. Chem. Soc. 115: 4461-4467; Piccirilli et al. (1991) Biochemistry 30: 10350-10356; Switzer et al. (1989) J. Am. Chem. Soc. 111: 8322-8323, the contents of all of which are hereby incorporated by reference in their entireties. A "non-conventional nucleotide" can also, in some embodiments, be a degenerate nucleotide or an intrinsically fluorescent nucleotide.

The term "non-extendable nucleotide," as used in regard to the various aspects and embodiments of the methods, assays, and kits described herein, refers to any nucleotide that prevents extension of a polynucleotide chain by a polymerase, including, but not limited to, a polymerase lacking 5' to 3' exonuclease activity described herein. Examples of such non-extendable nucleotides include dideoxy nucleotides (ddA, ddT, ddG, ddC) that lack a 3'-hydroxyl on the ribose ring, thereby preventing 3' extension by DNA polymerases. Other examples of such non-extendable nucleotides include, but are not limited to, inverted bases, which can be incorporated at the 3'-end of an oligo, leading to a 3'-3' linkage, which inhibits extension by DNA polymerases.

In some embodiments of the methods, assays, and kits described herein, a primer, such as a forward selective primer (or a reverse selective primer) comprises one or more locked nucleic acids. In some embodiments of the methods described herein, the 5' suppression sequence of the forward selective primer comprises one or more locked nucleic acids (LNAs). As used in regard to the various aspects and embodiments of the methods described herein, the term "LNA" or "locked nucleic acid" refers to any oligonucleotide containing one or more LNA monomer(s). An "LNA monomer," as the term is referred to herein is a nucleotide that comprises an O2'-C4'-methylene-linked bicyclic ribose unit that is locked in an RNA-like conformation. LNA is thus a structural mimic of RNA. LNA oligonucleotides can be synthesized by conventional automated synthesis to generate, for example, fully modified LNA, LNA-modified DNA, LNA-modified RNA or, for example, LNA-modified 2'-O-Me-RNA oligonucleotides. LNA oligonucleotides are characterized by their capability to bind to complementary nucleic acids with high binding affinities. As demonstrated herein, (see, for example, at FIG. 10), in some embodiments of the methods, assays, and kits provided herein, locked nucleic acids can be used to improve or increase suppression efficiency.

Selective Amplification of Target Nucleic Acids and Suppression of Non-Target Nucleic Acids The methods, assays, and kits described herein relate to the selective amplification of a target nucleic acid sequence of interest present in a sample comprising, for example, different, closely related variants of a nucleic acid sequence, by actively suppressing amplification of non-target nucleic acid sequences. This allows the methods, assays, and kits described herein to detect and identify the presence and/or amount of the target nucleic acid sequence in a nucleic acid sample, while suppressing amplification of related sequences. These methods and assays, and kits thereof, of selective amplification and suppression are particularly useful for amplification of highly related sequences that are difficult to distinguish by conventional PCR methods, such as, for example, sequences that are too similar in sequence to be able to identify distinct primer binding sequences that can be used to distinguish one from the other. The methods of tail-loop suppression PCR described herein, which utilize and incorporate a specific forward primer termed the "forward selective primer" and require the use of polymerases lacking 5' to 3' exonuclease activity, overcome these issues, and are suited for use in conjunction with existing PCR-based amplification methods or systems, as well as other applications such as next-generation sequencing, as described herein.

PCR methods provide an in vitro method for the enzymatic synthesis of specific nucleic acid sequences and use two oligonucleotide primers that hybridize to opposite strands and flank the region of interest in the target nucleic acid sequence, typically termed a "forward primer" and a "reverse primer," or together termed a "primer pair." A repetitive series of reaction steps involving template denaturation, primer annealing or hybridization, and extension of the annealed primers by a template-specific DNA polymerase results in exponential accumulation of a specific target nucleic acid fragment, the termini of which are defined by the 5' ends of each of the oligonucleotide primers in a primer pair. Typical PCR methods are capable of producing a selective enrichment of a specific DNA sequence by a factor of at least $10^9$. Methods of performing polymerase chain reaction (PCR) techniques are disclosed at a minimum in U.S. Pat. Nos. 4,683,202; 4,683,195; 4,800,159; and 4,965,188, and also described in Saiki et al., 1985, Science 230:1350, the contents of which are herein incorporated by reference in their entireties.

Briefly, in a typical PCR protocol, a nucleic acid sample having a target nucleic acid sequence to be amplified is denatured by heating the sample. In the presence of a nucleic acid polymerase and excess nucleoside triphosphates, oligonucleotide primers that hybridize specifically to the target sequence can prime new nucleic acid synthesis. Generally, oligonucleotide primers are added in vast excess compared to the nucleic acid to be amplified. Under the appropriate conditions, oligonucleotide primers hybridize to opposite strands of a denatured double-stranded nucleic acid sequence and are oriented with their 3' ends facing each other on the two strands, so that synthesis by a nucleic acid polymerase that catalyzes growth of new strands in the 5' to 3' direction extends across the segment of nucleic acid between these primers.

One round of extension and strand synthesis results in new strands of indeterminate length, which, like the parental strands, can hybridize to the primers upon a cycle of denaturation and annealing. These products accumulate only arithmetically with each subsequent cycle of denaturation, annealing to primers, and extension or synthesis. However, the second cycle of denaturation, annealing, and synthesis produces two single-stranded products that together compose a discrete double-stranded product that is exactly the length between the 5' ends of the primers. Each strand of this discrete product is complementary to one of the two primers and can therefore participate as a template in subsequent cycles. The amount of this product doubles with every subsequent cycle of synthesis, denaturation, and annealing, accumulating exponentially so that 30 cycles theoretically result in a $2^{28}$-fold (270 million-fold) amplification of the initial nucleic acid product.

The tail-loop suppression PCR methods and assays described herein generally follow the three steps characteristic of a typical PCR amplification cycle, i.e., "denaturation," "annealing" or "hybridizing," and "extension," but have specific and additional requirements at the hybridizing and extension steps to permit selective amplification of an amplification target sequence and active suppression of at least one suppression target sequence, as explained herein.

The methods and assays described herein for the selective amplification of an amplification target nucleic acid sequence or variant and suppression of a suppression target nucleic acid sequence require, in part, hybridization of a forward selective primer to a nucleic acid sample comprising, or presumed to comprise, an amplification target nucleic acid sequence to be amplified and a suppression target nucleic acid sequence to be suppressed.

Using the tail-loop suppression PCR methods and assays described herein, preferential exponential amplification of a target nucleic acid sequence, and suppression of a non-target nucleic acid sequence can be achieved using the forward selective primers described herein and amplification polymerases lacking 5' to 3' exonuclease activity.

Having obtained a nucleic acid sample suitable for use with the suppression PCR methods and assays described herein, the nucleic acid sample comprising or suspected to comprise a target nucleic acid sequence to be amplified is first denatured by heating the nucleic acid sample. A typical temperature for the denaturing step in a PCR cycle is at least 92° C., at least 93° C., at least 94° C., at least 95° C., at least 96° C., at least 97° C., at least 98° C., at least 99° C., or higher. The duration of the denaturing step in a typical PCR cycle is approximately 30 seconds, but can vary according to the sample, as understood by one of ordinary skill in the art. As used herein, "denaturation" or "nucleic acid melting" refers to the separation or unwinding of double-stranded nucleic acids and separation into single-stranded strands through the breaking of hydrogen bonding between complementary bases. Both terms are used herein to refer to the process as it occurs when a mixture is heated to a specific temperature, although "denaturation" can also refer to the separation of nucleic acid strands induced by chemicals like urea. It is preferred that complete strand separation occur during the denaturation step. Higher temperatures required for complete denaturation are associated with high GC content in the nucleic acids.

The methods and assays described herein for the selective amplification of an amplification target nucleic acid sequence or variant and suppression of a suppression target nucleic acid sequence require, in part, hybridization or annealing of a forward selective primer to a nucleic acid sample comprising, or suspected to comprise, an amplification target nucleic acid sequence and a suppression target sequence. As demonstrated herein, through the use of these forward selective primers, nucleic acid sequences that are highly similar to each other can be distinguished, and selective amplification of the amplification target nucleic acid sequence or variant and suppression of the suppression target nucleic acid sequence can be achieved, using a single pair of primers, i.e., the forward selective primer and a common reverse primer.

The "annealing" or "hybridization" step of a PCR cycle refers to the step where primers stably anneal to the template. Typically, primers with relatively low GC content (<50%) can require temperatures lower than 55° C. for full annealing, which can also increase the quantity of nonspecific products. For primers with high GC content, higher annealing temperatures can be tolerated.

Accordingly, the next step involves hybridization or annealing of the forward selective primer unique to the tail-loop suppression PCR methods and assays described herein to the nucleic acid sample comprising or suspected to comprise an amplification target nucleic acid sequence and a suppression target nucleic acid sequence, followed by extension of the hybridized forward selective primer.

The forward selective primer is designed to comprise a 3' end priming sequence that binds to a sequence shared by or common to both an amplification target sequence and a suppression target nucleic acid sequence (and thus acts as a common forward priming sequence or primer initiation site for extension by a 5' to 3' polymerase), as well as a 5' end suppression sequence that is identical to or substantially identical to a portion of the suppression target nucleic acid sequence but not to a portion of the amplification target nucleic acid sequence, thereby permitting selective suppression of the suppression target nucleic acid sequence during subsequent PCR cycles. It is preferred that the 5' suppression sequence of the forward selective primer is generally at least 8-10, e.g., at least 10 nucleotides in length, at least 15 nucleotides in length, at least 20 nucleotides in length, at least 30 nucleotides in length, at least 35 nucleotides in length, at least 40 nucleotides in length, at least 45 nucleotides in length, at least 50 nucleotides in length, at least 55 nucleotides in length, at least 60 nucleotides in length, at least 65 nucleotides in length, at least 70 nucleotides in length, at least 75 nucleotides in length, or more, in length. Accordingly, under annealing conditions for PCR amplification, the 3' end priming sequence of the forward selective primer hybridizes or anneals to the amplification target nucleic acid sequence or the suppression target nucleic acid sequence.

The annealed forward selective primer acts as a primer initiation site for extension by a 5' to 3' polymerase during the first round of annealing and extension in a tail-loop PCR cycle, and upon extension results in formation of hybridized duplexes comprising, in part, "complementary forward primer extension sequences" or "complementary extension sequences," as the terms are defined herein. These "complementary extension sequences" comprise, in the 5' to 3' direction, the forward selective primer sequence and a sequence complementary to the amplification target sequence, or the forward selective primer and a sequence complementary to the suppression target sequence. Accordingly, these hybridized duplexes generated during the extension cycle of the first cycle of tail-loop suppression PCR cycle comprise: (i) the amplification target sequence and a hybridized complementary extension sequence, such that the complementary extension sequence comprises, in the 5' to 3' direction, the forward selective primer sequence and a sequence complementary to the amplification target sequence, and (ii) the suppression target sequence and a hybridized complementary extension sequence, such that the complementary extension sequence comprises, in the 5' to 3' direction, the forward selective primer and a sequence complementary to the suppression target sequence.

Figure 16:
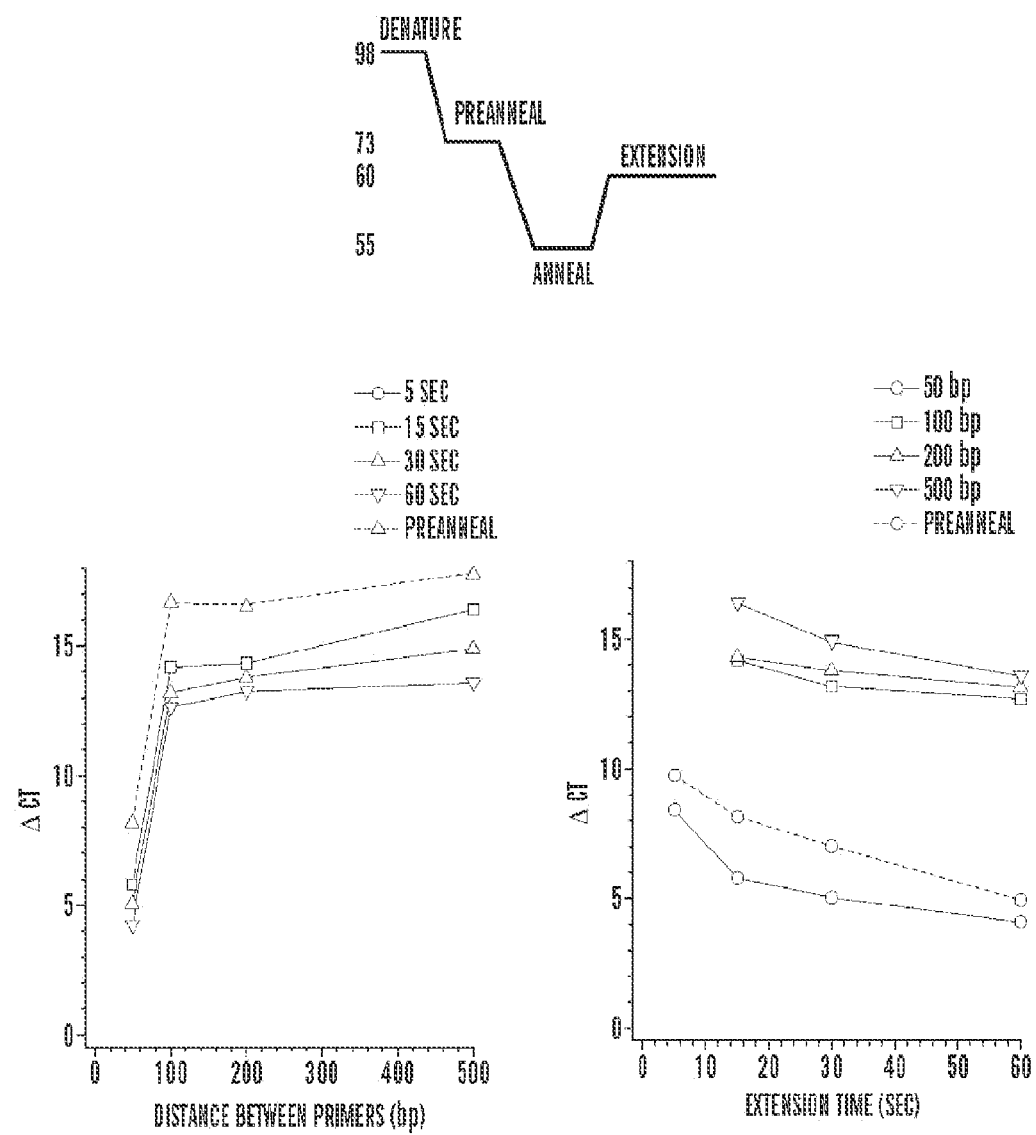
FIG. 16 demonstrates the relationship between suppression efficiency of the methods described herein and addition of a pre-annealing step.

In some embodiments of the methods and assays described herein, an additional pre-annealing step is added in which the temperature of the reaction mixture is reduced relative to the denaturation temperature but increased relative to the annealing temperature, which, as depicted in FIG. 16, can increase suppression efficiency of the methods and assays described herein.

The "extension" step of a PCR cycle refers to the step where the polymerase activity of a polymerase adds nucleotides to the 3'-OH of an annealed primer, thereby generating a strand complementary to the template nucleic acid. Accordingly, as used herein, "extending" refers to any enzyme-catalyzed, in vitro method for making a new strand of polynucleotide or elongating an existing polynucleotide or oligonucleotide (e.g., a forward selective primer or reverse primer) in a template-dependent manner. Extending a polynucleotide results in the incorporation of nucleotides into a polynucleotide (including nucleotides complementary to those in the template that comprise a spacer or span a gap), thereby forming an extended polynucleotide molecule complementary to the polynucleotide template. Extension can be performed at an elevated temperature to preserve specificity of hybridization, ensuring that only perfectly matched, i.e., completely complementary, sequences are extended by the polymerase. The extension temperature is chosen to be close to the optimal temperature for the polymerase being used, but is also chosen to be one at which the primers are prevented from dissociating, as known to one of ordinary skill in the art. For example, 72° C. is close to the optimal temperature for Taq DNA polymerase (~75° C.), but is a low enough temperature to prevent annealed primers from dissociating from the nucleic acid template. The duration of the extension step depends mainly on the length of the sequence to be amplified. Typically, a duration of 1 min per kb of target nucleic acid product length is sufficient. In some embodiments, a series of PCR cycles can end with a final and separate extension step that is longer, for example, 5-10 minutes to ensure completion of nucleic acid product synthesis.

In some embodiments of the methods and assays described herein, the extension step is at least 5 seconds long, e.g., preferably at least 6 seconds long, preferably at least 7 seconds long, preferably at least 8 seconds long, preferably at least 9 seconds long, preferably at least 10 seconds long, preferably at least 11 seconds long, preferably at least 12 seconds long, preferably at least 13 seconds long, preferably at least 14 seconds long, preferably at least 15 seconds long, preferably at least 20 seconds long, at least 30 seconds long, at least 40 seconds long, at least 50 seconds long, at least 60 seconds long, at least 90 seconds long, at least 120 seconds long, at least 150 seconds long, at least 180 seconds long, at least 210 seconds long, at least 240 seconds long, at least 270 seconds long, at least 300 seconds long, at least 330 seconds long, at least 360 seconds long, at least 390 seconds long, or more.

Following the first round or cycle of annealing and extension from the forward selective primer, subsequent amplification or suppression of PCR amplification is controlled both by the 5' end suppression sequence of the forward selective primer and the use of a polymerase lacking 5' to 3' exonuclease activity.

The complementary extension sequences, generated either by template-dependent 5' to 3' extension of the forward selective primer bound to the amplification target sequence or to the suppression target sequence, anneal to a common reverse primer that is complementary to a sequence shared by all complementary extension sequences generated by extension of the forward selective primer. In other words, the reverse primer used in the tail-loop suppression PCR methods and assays described herein is selected or designed to bind to a primer binding site that is shared or identical between a sequence complementary to the amplification target sequence and a sequence complementary to the suppression target sequence(s), according to principles of primer design known to one of ordinary skill in the art and as outlined herein.

The use of a polymerase lacking 5' to 3' exonuclease activity is critical during the extension of the reverse primer annealed to the sequence complementary to the amplification target sequence or to the sequence(s) complementary to the suppression target sequence(s). As described herein, the 5' end suppression sequence of a forward selective primer is designed to suppress amplification of any complementary extension sequences generated that comprise a sequence complementary to the target suppression sequence(s). Thus, as depicted in, for example, FIGS. 1 and 13, the complementary extension sequence generated from a suppression target nucleic acid sequence comprises the 5' end suppression sequence or "tail" of the forward selective primer. This 5' suppression sequence, which is substantially identical to a portion of the suppression target sequence, and is hence complementary to a portion of the complementary extension sequence of the suppression target sequence can hence form a "tail loop" or "stem loop" bound to the complementary extension sequence 3' of the forward primer binding site. The binding of the 5' end suppression sequence to a portion of the complementary extension sequence generated from the suppression target sequence(s) and formation of a tail-loop prevents further extension of the reverse primer when using a polymerase lacking 5' to 3' exonuclease, thus resulting in a shortened reverse primer extension sequence that does not extend the entire length of the complementary extension sequence and does not provide a forward selective primer binding site during subsequent PCR cycles. Accordingly, amplification of the suppression target sequence(s) is suppressed and does not undergo exponential amplification.

In contrast, because the 5' suppression sequence is selected so that it does not share substantial identity with the amplification target sequence, and is not complementary to a portion of the complementary extension sequence of the amplification target sequence, a "tail loop" does not form on the complementary extension sequence generated from the amplification target sequence. Accordingly, extension of the reverse primer using a polymerase lacking 5' to 3' exonuclease activity extends across the entire length of the complementary extension sequence generated from the amplification target sequence and provides a forward selective primer binding site during subsequent PCR cycles. Thus, amplification of the amplification target sequence is not suppressed and undergoes exponential amplification. Amplification of the suppressed sequence would be preferably or at best cubic or quadratic.

Because suppression of amplification depends upon the substantial blockade of advance of polymerase-catalyzed synthesis caused by hybridization of a suppression sequence to a template, the methods, assays and kits described herein rely upon the substantial inability of the advancing polymerase to either degrade or displace an oligonucleotide hybridized in its path. Thus, a polymerase applicable for the various aspects and embodiments of the methods, assays, and kits for suppression PCR described herein should substantially lack 5'-3' exonuclease activity that could degrade a primer hybridized in the way of the advancing polymerase. Polymerases fulfilling this criterion are known to those of ordinary skill in the art and are readily commercially available. Further, to the extent that a polymerase that substantially lacks 5'-3' exonuclease activity is able to simply displace, rather than degrade, a sequence hybridized in its path, it is preferred that a polymerase for use in the suppression described herein substantially lack or have very low strand displacement activity.

The efficiency of suppression achieved using the methods described herein can be expressed, for example, by the "change of threshold cycle," or "$\Delta C_T$" or, alternatively, by the term "equivalent cycle of suppression." Threshold cycle or $C_T$ is understood in the art to be the cycle at which a PCR product or amplicon crosses a pre-determined threshold of product or amplicon detection over background. In an unsuppressed amplification, $C_T$ is proportional to the initial amount of amplification template. For the methods and assays disclosed herein, $\Delta C_T$ is a measure of the increase in $C_T$ for detection of a suppressed PCR product. That is, suppression will increase the number of PCR cycles required to detect the suppressed product over background. The more efficient the suppression relative to unsuppressed amplification, the greater the $\Delta C_T$. The alternative expression "equivalent cycle of suppression" is substantially the same, expressing the number of cycle differences between detection in the suppressed versus the unsuppressed state. Equivalent cycles of suppression also permit the calculation of a "suppression factor," which is based on the ideal amplification efficiency where each cycle leads to a doubling of available template. For example, an equivalent cycles of suppression value of 3 cycles translates to a suppression factor of $2^3=8$, i.e., without suppression there could have been 8× as much amplicon product derived from the suppression target sequence. An equivalent cycles of suppression value of 4 cycles translates to a suppression factor of $2^4=16$. See the comparison of suppression techniques at FIG. 14 for further illustration.

A "polymerase," as used in regard to various aspects and embodiments of the methods, assays, and kits described herein, refers to an enzyme that catalyzes polynucleotide synthesis by addition of nucleotide units to a nucleotide chain using DNA or RNA as a template. The term refers to either a complete enzyme as it occurs in nature, or an isolated, active catalytic domain, fragment, or to an engineered variant thereof. Generally, polymerase enzymes initiate synthesis at the 3'-end of a primer or oligonucleotide, such as a forward selective primer or a reverse primer, annealed or hybridized to a nucleic acid sequence, and proceeds in the 5'-direction along the nucleic acid to synthesize a strand complementary to the nucleic acid to which it is hybridized until synthesis terminates. "Nucleic acid polymerases," as used herein, refer to a broad class of enzymes that catalyze the polymerization of individual nucleotides, e.g., deoxyribonucleotides and ribonucleotides, into a nucleic acid strand or polynucleotide in a template-dependent manner. Nucleic acid polymerases include reverse transcriptases, DNA polymerases, RNA polymerases, and mutant or altered forms of any of the foregoing. In some embodiments of the aspects described herein, the enzyme having polymerase activity can comprise a hybrid protein. The term "hybrid protein" is used herein to describe a protein that comprises amino acid residues from more than one parent sequence. Examples of hybrid polymerase proteins and methods of generating hybrid proteins are disclosed in WO2004011605, the contents of which are herein incorporated in their entirety by reference. Such polymerases are therefore non-naturally occurring variants of polymerases.

As used in regard to various aspects and embodiments of the methods, assays, and kits described herein, the terms "5' to 3' exonuclease" or "5' to 3' exonuclease activity" refers to a protein or domain of, or a protein activity of, a protein that catalyzes the stepwise removal of mononucleotides or short oligonucleotides, e.g., 2 nucleotides to 3 nucleotides long, from 5'-termini of nucleic acid molecules. "5' to 3' exonuclease activity" includes a 5' to 3' exonuclease activity traditionally associated with some DNA polymerases whereby nucleotides are removed from the 5' end of an oligonucleotide annealed to a template or target nucleic acid in a sequential manner.

Accordingly, as used in regard to the various aspects and embodiments of the methods, assays, and kits described herein, a "polymerase lacking 5' to 3' exonuclease activity" or a "5' to 3' exo minus polymerase" refers to any polymerase lacking the enzymatic activity to catalyze the stepwise removal of mononucleotides or short oligonucleotides from 5'-termini of nucleic acid molecules or, more specifically, remove nucleotides from the 5' end of an oligo- or polynucleotide annealed to a template nucleic acid. At a minimum, a polymerase used in the reverse primer extension step as described herein must lack 5' to 3' exonuclease activity. In general, it is practical to use a 5' to 3' exo minus polymerase for both forward selective primer and reverse primer extension steps of the methods described herein. The lack of 5' to 3' exonuclease activity prevents removal of the 5' suppression sequence bound to the complementary extension sequence of suppression target sequence(s) during extension from the reverse primer. A variety of DNA polymerases lacking 5' to 3' exonuclease activity are commercially available and known to those of ordinary skill in the art. Non-limiting examples of polymerases lacking 5' to 3' exonuclease activity include: SSOFAST, Pfx polymerase, KOD1, IPROOF, PHIRE, PHUSION, and any thermostable DNA polymerase mutants or variants lacking 5' to 3' exonuclease activity.

Further, to the extent that a polymerase that substantially lacks 5'-3' exonuclease activity is able to simply displace, rather than degrade, a sequence hybridized in its path, it is preferred that a polymerase for use in the suppression described herein also substantially lacks or have very low strand displacement activity. By "very low strand displacement activity" is meant that the polymerase has no more than 50% more strand displacement activity, and preferably no more than 40% more, no more than 30% more, no more than 25% more, no more than 20% more, no more than 15% more, no more than 10% more, no more than 5% more, no more than 4% more, no more than 3% more, no more than 2% more, or no more than 1% more strand displacement activity than SSOFAST polymerase, and more preferably, less than 90%, less than 80%, less than 70%, less than 60%, less than 50%, less than 40%, less than 30%, less than 20%, less than 10%, less than 5% of the strand displacement activity of SSOFAST polymerase, up to and including a complete lack of strand displacement activity as, for example, can be determined by using the polymerase in a strand displacement assay such as those described, e.g., in U.S. Pat. No. 6,642,034, or in a primer-block assay described, e.g., in Kong et al., J. Biol. Chem. 268:1965-1975 (1993). In no instance can the strand displacement activity of the polymerase used by as high as that of Bst1 polymerase.

It is preferred that the polymerases lacking 5' to 3' exonuclease activity used in the various aspects and embodiments of the methods, assays, and kits described herein are also thermostable. As used herein, the term "thermostable nucleic acid polymerase" refers to an enzyme that is relatively stable to heat when compared, for example, to nucleic acid polymerases from $E.$ $coli$, and which catalyzes the template-dependent polymerization of nucleoside triphosphates. A "thermostable nucleic acid polymerase," as the term is used herein, retains enzymatic activity for polymerization when subjected to the repeated heating and cooling cycles used in PCR. Preferably, a "thermostable nucleic acid polymerase" has optimal activity at a temperature above 45° C. Thermostable polymerases useful for e.g., PCR and related methods are well known to those of skill in the art and are widely available.

It is preferred that polymerases lacking 5' to 3' exonuclease activity for use in the various aspects and embodiments of the methods, assays, and kits described herein have low error rates or high fidelity. As used herein, the "error rate" of a DNA polymerase refers to the number of incorrect, i.e., non-complementary bases, a DNA polymerase adds to a sequence being synthesized per 10000 nucleotides added per replication cycle. For example, the error rate of Taq polymerase was initially estimated at $2 \times 10^{-4}$ nucleotides/cycle (Saiki et al., 1988). Typically, polymerases with 3' to 5' exonuclease activity have low error rates, but can sometimes have decreased yields. Accordingly, in some embodiments, a polymerase for use in the methods described herein has 3' to 5' exonuclease activity. In other embodiments, the polymerase has no 3' to 5' exonuclease activity.

Methods of Detection of Amplification Target Sequences

Methods, systems, and devices for detecting and quantifying amplified PCR products are well known in the art and any of them can be used in conjunction with the methods described herein. Examples of such methods and systems include real-time PCR with detection of amplified nucleic acid sequences with fluorescent dyes binding to double stranded DNA, such as SYBR Green or ethidium bromide, Real-time PCR with molecular beacons (detecting binding of fluorescently labeled probes to adjacent sequence in amplified PCR products), using Real-Time PCR thermocyclers such as the LIGHTCYCLER system from Roche (Indianapolis, Ind.), Applied Biosystems 7900HT, 7300, 7500 Real-time PCR systems (Foster City, Calif.), 1-cycler from Bio-rad (Hercules, Calif.), ROTORGENE Real-time PCR cycler from Corbett (Sydney, Australia) and others.

Amplification target sequence PCR products or amplicons generated according to the methods and assays described herein can also be separated and quantified by size separation methods, such as electrophoresis methods, e.g., gel electrophoresis and capillary electrophoresis. Size separation of nucleic acids is well known, e.g., by agars or polyacrylamide electrophoresis or by column chromatography, including HPLC separation. Methods for separating and detecting the presence or amount of polynucleotides are well known in the art and any of them can be used in the methods described herein so long as they are capable of separating individual polynucleotides by at least the difference in length between an amplification product generated from an amplification target sequence, and any amplification products generated from a suppression target sequence(s). Useful methods for the separation and analysis of amplified products include, but are not limited to, electrophoresis (e.g., slab gel or capillary electrophoresis (CE)), chromatography (dHPLC), and mass spectrometry).

In some embodiments of the assays and methods of tail-loop suppression PCR described herein, methods and systems that permit detection and monitoring of the amplification of two or more nucleic acid sequences within the same reaction tube are applied. Such methods typically involve determination of a threshold cycle or Ct, as the term is defined herein. By determining the "threshold cycle" or "Ct" at which the signal corresponding to a specific amplified sequence, reaches or passes a predetermined threshold, and comparing this with the Ct values recorded for known nucleic acid sequences present at known concentrations, either in control samples processed in parallel with a test sample, or in a test sample itself following the addition of such known nucleic acid sequences prior to the initiation of the test procedure, the concentration of each amplified product, i.e., an extended complementary sequence amplicon generated from an amplification target sequence, can be reliably estimated, as demonstrated herein. As shown herein, the methods and assays for tail-loop suppression PCR described herein permit increased detection of a rare variant sequence desired to be amplified from among a plurality of similar, related variant sequences present in much greater quantities, and results in a greatly increased threshold cycle at which the suppressed variant sequence(s) can be detected.

Applications of Tail-Loop Suppression PCR Methods

The suppression PCR methods described herein are useful for a variety of applications in which amplification and detection of a rare sequence variant, despite the presence of even a large number of similar, sequence-related non-target nucleic acid variants, is required. Accordingly, provided herein in some aspects and embodiments are assays and kits for the detection of amplification target sequences for use in cancer screening applications, personalized medicine applications, environmental applications, agricultural applications, food contamination applications, and the like.

Provided herein, in some aspects, are assays or in vitro assays for detecting the presence of one of two or more variants of a nucleic acid sequence in a nucleic acid sample. Such assays comprise:

(a) hybridizing a forward selective primer to a nucleic acid sample comprising an amplification target sequence and a suppression target sequence, such that the forward selective primer comprises: (i) a 3' end priming sequence that is fully complementary and hybridizes to a portion of the amplification target sequence and the suppression target sequence, and (ii) a 5' end suppression sequence that is substantially identical to a portion of the suppression target sequence, such that the portion of the suppression target to which the 5' suppression sequence is substantially identical is 5' of the portion of the suppression target sequence to which the 3' end priming sequence hybridizes;

(b) extending the hybridized forward selective primer of step (a) using polymerase enzyme that, the extension generating hybridized duplexes comprising: (i) the amplification target sequence and a hybridized complementary extension sequence, where the complementary extension sequence comprises, in the 5' to 3' direction, the forward selective primer and a sequence complementary to the amplification target sequence, and (ii) a suppression target sequence and a hybridized complementary extension sequence, wherein the complementary extension sequence comprises, in the 5' to 3' direction, the forward selective primer and a sequence complementary to the suppression target sequence;

(c) denaturing the hybridized duplexes of step (b) to separate target sequences and complementary extension sequences; and (d) hybridizing a reverse primer to the complementary extension sequences of step (c), and extending the hybridized reverse primer using a 5' to 3' polymerase that lacks 5' to 3' exonuclease activity, such that if the complementary extension sequence comprises the sequence complementary to the suppression target sequence, then amplification is suppressed because of tail loop formation by the '5' suppression sequence and a shorter amplification product is generated, and if the complementary extension sequence comprises the sequence complementary to the amplification target sequence, then amplification is not suppressed and a longer amplification product is generated, allowing the presence of one of two or more variants of a nucleic acid sequence to be detected.

In some embodiments of these assays and all such assays described herein, steps (a)-(d) are repeated at least 10 times.

In some embodiments of these assays and all such assays described herein, the forward selective primer is at least 30 nucleotides in length.

In some embodiments of these assays and all such assays described herein, the 5' end suppression sequence is at least 10 nucleotides in length.

In some embodiments of these assays and all such assays described herein, the longer amplification product generated in step (d) is at least 40 nucleotides in length.

In some embodiments of these assays and all such assays described herein, the extending of the hybridized reverse primer using the 5' to 3' polymerase that lacks 5' to 3' exonuclease activity of step (d) occurs for at least 5 seconds or more.

In some embodiments of these assays and all such assays described herein, the forward selective primer further comprises a loop sequence, where the loop sequence is 5' of the 3' end priming sequence and does not comprise a sequence complementary to the complementary extension sequences. In some such embodiments, the loop sequence is at least 2 nucleotides in length.

In some embodiments of these assays and all such assays described herein, the nucleic acid sample is a DNA sample.

In some embodiments of these assays and all such assays described herein, the forward selective primer comprises one or more locked nucleic acids (LNAs).

In some embodiments of these assays and all such assays described herein, the 5' suppression sequence comprises one or more locked nucleic acids (LNAs).

Also provided herein, in some aspects, are multiplex assays or multiplex in vitro assays for detecting the presence of multiple, different target nucleic acid variants in a nucleic acid sample. Such assays can be designed to comprise two or more or multiple forward selective primers, each of which is specific for a different target nucleic acid variant, such as, for example, two different gene variants. By using multiple forward selective primers, simultaneous detection of different target nucleic acid sequences can be achieved even when each of the different target nucleic acid sequences is a variant of other closely related variant sequences. In some aspects, the assays comprise:

(a) hybridizing two or more forward selective primers to a nucleic acid sample comprising two or more amplification target sequences and two or more suppression target sequences, such that each of the forward selective primers comprises: (i) a 3' end priming sequence that is fully complementary and hybridizes to a portion of the amplification target sequence and the suppression target sequence, and (ii) a 5' end suppression sequence that is substantially identical to a portion of the suppression target sequence, such that the portion of the suppression target to which the 5' suppression sequence is substantially identical is 5' of the portion of the suppression target sequence to which the 3' end priming sequence hybridizes;

(b) extending each of the hybridized forward selective primers of step (a) using a polymerase enzyme, the extension generating hybridized duplexes comprising: (i) the amplification target sequence and a hybridized complementary extension sequence, where the complementary extension sequence comprises, in the 5' to 3' direction, the forward selective primer and a sequence complementary to the amplification target sequence, and (ii) a suppression target sequence and a hybridized complementary extension sequence, wherein the complementary extension sequence comprises, in the 5' to 3' direction, the forward selective primer and a sequence complementary to the suppression target sequence;

(c) denaturing the hybridized duplexes of step (b) to separate target sequences and complementary extension sequences; and (d) hybridizing two or more reverse primers to the complementary extension sequences of step (c), and extending the hybridized reverse primers using a 5' to 3' polymerase that lacks 5' to 3' exonuclease activity, such that if the complementary extension sequence comprises the sequence complementary to the suppression target sequence, then amplification is suppressed because of tail loop formation by the '5' suppression sequence and a shorter amplification product is generated, and if the complementary extension sequence comprises the sequence complementary to the amplification target sequence, then amplification is not suppressed and a longer amplification product is generated, allowing the presence of multiple target nucleic acid variants of a nucleic acid sequence to be detected.

In some embodiments of these aspects and all such aspects described herein, the assay is a cancer screening assay. When used as a cancer screening assay, mutations or other epigenetic changes, such as methylation, in nucleic acid sequences that are known to arise de novo in cancer patients, for example, are selected as amplification target sequence(s) to be detected using one or more forward selective primers. Accordingly, the 5' suppression sequence of the forward selective primer is designed to suppress amplification of the wild-type or 'normal' sequence found in the patient's non-tumor cells, allowing the amplification target sequence, found only in cancer or tumor cells, to be detected, even when present in small amounts in a sample, such as, for example, a blood sample. In some embodiments of these assays, a control sample for the assay is a normal tissue or cell population obtained from the individual being screened. For example, the primary chromosome anomaly in Burkitt's lymphoma is a translocation t(8;14)(q24;q32), found in 60-70% of the cases. Variant translocations having in common an 8q24 break, i.e., the t(8;22)(q24;q11) and t(2;8)(p12;q24) occur in approximately 10-15% and 2-5% of cases, respectively. These translocations juxtapose IgH sequences and the c-MYC oncogene. Accordingly, in those embodiments of the cancer screening assays directed to screening for Burkitt's lymphoma, for example, the sequence of the translocation junction point between the IgH sequences and the c-MYC oncogene can serve as the amplification target sequence. Similarly, known spontaneous mutations that arise in or are associated with other oncogenes, such as RAS gene family mutations and p53 mutations, that are frequently mutated in human tumors, such as adenocarcinomas of the pancreas, colon, and lung, can be selected as amplification target sequences to be detected using the cancer screening assays described herein. Spontaneous mutations have also been demonstrated to occur in the PREX2 gene in melanomas, which can also be selected as amplification target sequences for use in the cancer screening assays described herein. In some embodiments of these cancer screening assays, the cancer screening assay is a multiplex assay that can detect the presence of two or more amplification target sequences.

In some embodiments of these aspects and all such aspects described herein, the assay is a personalized cancer recurrence detection assay. When used as a cancer recurrence detection assay, sequence differences, such as mutations or other epigenetic changes, such as methylation, in nucleic acid sequences that are identified in a patient's tumor cell are exploited to design a personalized forward selective primer with a 5' suppression sequence targeting the wild-type sequence and permitting efficient amplification only of the patient's tumor variant sequence. In some embodiments of such assays, a control sample for the assay is a normal tissue or cell population obtained from the individual being screened. Periodic monitoring of blood or other tissue samples can identify a tumor recurrence at an early stage using such assays. In some embodiments of these personalized cancer recurrence detection assays, the personalized cancer recurrence detection assay is a multiplex assay that can detect the presence of two or more amplification target sequences.

Accordingly, in some embodiments of these cancer screening assays and personalized cancer recurrence detection assays, the amplification target sequence comprises a mutation or epigenetic modification found in cancer cells, but not in normal cells. In some embodiments of these assays, a control sample for the assay is a normal tissue or cell population obtained from the individual being screened.

In some embodiments of these cancer screening assays and personalized cancer recurrence detection assays, the nucleic acid sample is obtained from a blood sample.

Non-limiting examples of cancers for which the cancer screening assays described herein can be applied include basal cell carcinoma; biliary tract cancer; bladder cancer; bone cancer; brain and CNS cancer; breast cancer; cervical cancer; choriocarcinoma; colon and rectum cancer; connective tissue cancer; cancer of the digestive system; endometrial cancer; esophageal cancer; eye cancer; cancer of the head and neck; gastric cancer; intra-epithelial neoplasm; kidney cancer; larynx cancer; leukemia; liver cancer; lung cancer (e.g., small cell and non-small cell); lymphoma including Hodgkin's and non-Hodgkin's lymphoma; melanoma; myeloma; neuroblastoma; oral cavity cancer (e.g., lip, tongue, mouth, and pharynx); ovarian cancer; pancreatic cancer; prostate cancer; retinoblastoma; rhabdomyosarcoma; rectal cancer; cancer of the respiratory system; sarcoma; skin cancer; stomach cancer; testicular cancer; thyroid cancer; uterine cancer; cancer of the urinary system, as well as other carcinomas and sarcomas.

Spontaneous, epigenetic mutations have also been shown to be associated with other disorders, such as autism and autism spectrum disorders. Accordingly, in some embodiments of these aspects and all such aspects described herein, the assay is an autism screening assay. When used as a autism screening assay, mutations or other epigenetic changes, such as methylation, in nucleic acid sequences that are known to arise de novo in subjects having or at risk for autism, for example, are selected as amplification target sequence(s) to be detected. For example, spontaneous mutations in FOXP1 or GRIN2B that have been associated with autism can be selected. Accordingly, the 5' suppression sequence of the forward selective primer is designed to suppress amplification of the wild-type or 'normal' sequence found in the majority of the patient's cells, allowing the amplification target sequence, found only in cells with the mutation, to be detected, even when present in small amounts in a sample, such as, for example, a blood or cerebrospinal fluid sample.

The assays described herein are also useful in the detection, screening, and/or monitoring of variant sequences associated with genetic disorders, such as during fetal development. Accordingly, in some embodiments of these aspects and all such aspects described herein, the assay is a prenatal genetic detection assay. When used as a prenatal genetic detection assay, sequence differences, such as insertions, deletions, substitutions, and polymorphisms, in nucleic acid sequences that are known to be associated with one or more genetic disorders or diseases can be screened for and identified by designing a forward selective primer with a 5' suppression sequence targeting the maternal gene sequence(s), thus permitting efficient amplification only of any variant sequences associated with a genetic disorder(s) present in fetal cells, which are found in low amounts in the maternal circulation. By permitting selective amplification of sequences in the low amounts of fetal cells present in the maternal circulation, the methods and assays described herein avoid or reduce the need for obtaining amniotic fluid samples, and the risks associated therein. Exemplary monogenic disorders that can be screened for using embodiments of the prenatal screening assays described herein include, but are not limited to, ADA deficiency, cystic fibrosis, familial-hypercholesterolemia, hemophilia, chronic ganulomatous disease, Duchenne muscular dystrophy, Fanconi anemia, sickle-cell anemia, Gaucher's disease, Hunter syndrome, and X-linked SCID.

In some embodiments of these aspects and all such aspects described herein, the assay is a microbial detection assay. When used as a microbial detection assay, sequence differences, such as insertions, deletions, substitutions, and polymorphisms, occurring between related species or subspecies of a microorganism, such as a bacterial species or viral strain, can be used to detect the presence of a minor species or rare species within a population of related dominant species. Accordingly, the 5' suppression sequence of the forward selective primer is designed to suppress amplification of sequences from the dominant species found in the sample, allowing amplification of the minor species. Such microbial detection assays are useful, for example, when examining microbial populations obtained from a gut or intestinal sample (i.e., gut flora), as well as, examining microbial populations in environmental samples, to detect for the presence of a minor species that is pathogenic, or antibiotic resistant, for example.

The assays described herein are also applicable for detecting or identifying contaminations or infections in the food and agriculture industries. Accordingly, in some embodiments of these aspects and all such aspects described herein, the assay is a genetically modified organism detection assay. When used as a genetically modified organism detection assay, sequence differences, such as insertions, deletions, polymorphisms, etc., occurring between a related wild-type organism and a genetically modified organism (including plants as well as animals), can be used to detect the presence of a genetically modified organism within a sample comprising a majority of nucleic acid sequences derived from wild-type, non-genetically modified organisms. Accordingly, the 5' suppression sequence of the forward selective primer is designed to suppress amplification of sequences from wild-type, non-genetically modified organisms species found in the sample, allowing amplification of sequences from genetically modified organisms. Another embodiment of the assays described herein for detecting rare sequences, such as contamination or infections, in the food and agriculture industries are assays for characterizing gut content(s) of fish to identify and distinguish between farmed or harvested fish and fish caught in the wild or "prey characterization assays."

Assays based on tail-loop suppression PCR methods described herein are also useful for suppression of dimer amplification during nucleic-acid based library constructions for next generation sequencing applications. During construction of nucleic acid-based libraries, such as, for example, microRNA libraries, or genomic libraries, common adaptor sequences are used to flank a nucleic acid insert of interest, to permit rapid cloning and ligation, and allow easy amplification of insert sequences using common primers specific for the adaptor sequences. However, the adaptor sequences can also form adaptor dimers lacking an insert sequence, or can insert undesirable sequences, such as carrier nucleic acid sequences (see, for example, FIG. 15). Thus, upon amplification using primers specific for the adaptor sequences, adaptor dimers, as well as undesirable sequences, such as carrier nucleic acid sequences, are amplified in addition to the desired insert sequences. Using the methods and assays described herein, however, specific suppression of amplification of adaptor dimers or, for example, carrier sequences can be achieved. Accordingly, in some embodiments, the assay is a library construction assay. When used as a library construction assay, sequence differences occurring due to the formation of a unique "adaptor-adaptor" junction, or, in the case of a ligated carrier sequence, unique sequences of the carrier sequence, are exploited to design a forward selective primer with a 5' suppression sequence targeting the adaptor-adaptor junction sequence, or the carrier sequence, thus permitting efficient amplification only of adaptor sequences flanking a desired insert sequence.

Also provided herein, in some aspects, are kits for the selective amplification of specific species or variants of nucleic acid sequences within an excess of unwanted similar sequences or variants, which are actively suppressed, using the methods and assays described herein.

Accordingly, in some aspects and embodiments, a kit, as described herein, provides at least one forward selective primer and a reverse primer. A kit can include any combination of components that are necessary to facilitate any method described herein. The options for components of the kits are not particularly limited or restricted, e.g., with regard to specific oligonucleotide sequence, which can be chosen on the basis of the amplification target and the suppression target involved. Kits can also include other primers necessary for preparing a nucleic acid sample for use in any of the methods described herein, for example, one or more reverse-transcription primers, other amplification primer pairs, or combinations thereof. Kits for use with the methods described herein can optionally contain written instructions describing how to use the kit and/or how to conduct the methods provided herein. Kits can also provide enzymes necessary for the methods described herein, e.g., thermostable DNA polymerases lacking 5' to 3' exonuclease activity.

Accordingly, in some aspects, provided herein are kits comprising at least one forward selective primer, the forward selective primer comprising: (i) a 3' end priming sequence that is fully complementary and hybridizes to a portion of an amplification target sequence and at least one suppression target sequence, and (ii) a 5' end suppression sequence that is substantially identical to a portion of the at least one suppression target sequence, such that the portion of the at least one suppression target to which the 5' suppression sequence is substantially identical is 5' of the portion of the suppression target sequence to which the 3' end priming sequence hybridizes. Polymerase extension of the forward selective primer from the 3' end priming sequence forms or generates a complementary extension sequence comprising the forward selective primer and a sequence complementary to the amplification target sequence, or comprising the forward selective primer and a sequence complementary to the suppression target sequence.

In some embodiments of the kits, the kit further comprises a reverse primer that can bind or hybridize to a shared or common site on the complementary extension sequence generated from both the target amplification sequence and the suppression target sequence(s). Extension using a thermostable DNA polymerase lacking 5' to 3' exonuclease activity from the reverse primer is blocked by the 5' end suppression sequence hybridized to a portion of the complementary extension sequence of the suppression target sequence(s), i.e., the formation of a tail loop. In the case of the complementary extension sequence generated from the amplification target sequence, extension using a thermostable DNA polymerase lacking 5' to 3' exonuclease activity from the reverse primer hybridized to the complementary extension sequence is not blocked, and extends to the end of the forward selective primer.

In some embodiments of these kits, the kit further comprises a thermostable DNA polymerase lacking 5' to 3' exonuclease activity. In some embodiments, the thermostable DNA polymerase lacking 5' to 3' exonuclease activity substantially lacks strand displacement activity.

Some aspects and embodiments disclosed herein can be illustrated by, for example, any of the following numbered paragraphs:

1. A method of detecting the presence of one of two or more variants of a nucleic acid sequence in a nucleic acid sample, the method comprising:
   (a) hybridizing a forward selective primer to a nucleic acid sample comprising an amplification target sequence and a suppression target sequence, wherein the forward selective primer comprises: (i) a 3' end priming sequence that is complementary to and hybridizes to a portion of the amplification target sequence and the at least one suppression target sequence, and (ii) a 5' end suppression sequence that is substantially identical to a portion of the suppression target sequence, wherein the portion of the suppression target to which the 5' suppression sequence is substantially identical is 5' of the portion of the suppression target sequence to which the 3' end priming sequence hybridizes;
   (b) extending the hybridized forward selective primer of step (a) using a polymerase enzyme, the extension generating hybridized duplexes comprising: (i) the amplification target sequence and a hybridized complementary extension sequence, wherein the complementary extension sequence comprises, in the 5' to 3' direction, the forward selective primer and a sequence complementary to the amplification target sequence, and (ii) the suppression target sequence and a hybridized complementary extension sequence, wherein the complementary extension sequence comprises, in the 5' to 3' direction, the forward selective primer and a sequence complementary to the suppression target sequence;
   (c) denaturing the hybridized duplexes of step (b) to separate target sequences and complementary extension sequences; and
   (d) hybridizing a reverse primer to the complementary extension sequences of step (c), and extending the hybridized reverse primer using a 5' to 3' polymerase that lacks 5' to 3' exonuclease activity and substantially lacks strand displacement activity, wherein if the complementary extension sequence comprises the sequence complementary to the suppression target sequence, then amplification is suppressed by formation of a stem loop by the 5' suppression sequence and a shorter amplification product is generated, and wherein if the complementary extension sequence comprises the sequence complementary to the amplification target sequence, then amplification is not suppressed by formation of a stem loop and a longer amplification product is generated, whereby the presence of one of two or more variants of a nucleic acid sequence is detected.
2. The method of paragraph 1, wherein steps (a)-(d) are repeated at least 10 times.
3. The method of any one of paragraphs 1-2, wherein the forward selective primer is at least 30 nucleotides in length.
4. The method of any one of paragraphs 1-3, wherein the 5' end suppression sequence is at least 10 nucleotides in length.
5. The method of any one of paragraphs 1-4, wherein the longer amplification product generated in step (d) is at least 40 nucleotides in length.
6. The method of any one of paragraphs 1-5, wherein the extending of the hybridized reverse primer using the 5' to 3' polymerase that lacks 5' to 3' exonuclease activity and substantially lacks strand displacement activity of step (d) occurs for at least 5 seconds or more.
7. The method of any one of paragraphs 1-6, wherein the forward selective primer further comprises a loop spacer sequence, wherein said loop sequence is 5' of the 3' end priming sequence and does not comprise a sequence complementary to the complementary extension sequences.
8. The method of paragraph 7, wherein the loop spacer sequence is at least 3 nucleotides in length.
9. The method of any one of paragraphs 1-8, wherein the reverse primer is a reverse selective primer.
10. The method of paragraph 9, wherein the reverse selective primer targets a different suppression target sequence than the forward selective primer.
11. The method of any one of paragraphs 1-10, wherein the nucleic acid sample is a DNA sample.
12. The method of any one of paragraphs 1-11, wherein the forward selective primer comprises one or more locked nucleic acids (LNAs).
13. The method of any one of paragraphs 1-12, wherein the 5' suppression sequence of the forward selective primer comprises one or more locked nucleic acids (LNAs).
14. The method of any one of paragraphs 1-13, wherein the suppression target sequence is an artifact sequence of a library construction sequence.
15. The method of paragraph 14, where the artifact is an adapter dimer or a carrier nucleic acid attached to adapters.
16. An assay for detecting the presence of one of two or more variants of a nucleic acid sequence in a nucleic acid sample, the assay comprising:
   (a) hybridizing a forward selective primer to a nucleic acid sample comprising an amplification target sequence and a suppression target sequence, wherein the forward selective primer comprises: (i) a 3' end priming sequence that is complementary to and hybridizes to a portion of the amplification target sequence and the at least one suppression target sequence, and (ii) a 5' end suppression sequence that is substantially identical to a portion of the suppression target sequence, wherein the portion of the at least one suppression target to which the 5' suppression sequence is substantially identical is 5' of the portion of the suppression target sequence to which the 3' end priming sequence hybridizes;
   (b) extending the hybridized forward selective primer of step (a) using a polymerase enzyme, the extension generating hybridized duplexes comprising: (i) the amplification target sequence and a hybridized complementary extension sequence, wherein the complementary extension sequence comprises, in the 5' to 3' direction, the forward selective primer and a sequence complementary to the amplification target sequence, and (ii) the suppression target sequence and a hybridized complementary extension sequence, wherein the complementary extension sequence comprises, in the 5' to 3' direction, the forward selective primer and a sequence complementary to the suppression target sequence;

(c) denaturing the hybridized duplexes of step (b) to separate target sequences and complementary extension sequences; and (d) hybridizing a reverse primer to the complementary extension sequences of step (c), and extending the hybridized reverse primer using a 5' to 3' polymerase that lacks 5' to 3' exonuclease activity and substantially lacks strand displacement activity, wherein if the complementary extension sequence comprises the sequence complementary to the suppression target sequence, then amplification is suppressed by formation of a stem loop by the 5' suppression sequence and a shorter amplification product is generated, and wherein if the complementary extension sequence comprises the sequence complementary to the amplification target sequence, then amplification is not suppressed by formation of a stem loop and a longer amplification product is generated, whereby the presence of one of two or more variants of a nucleic acid sequence is detected.

17. The assay of paragraph 16, wherein steps (a)-(d) are repeated at least 10 times.

18. The assay of any one of paragraphs 16-17, wherein the forward selective primer is at least 30 nucleotides in length.

19. The assay of any one of paragraphs 16-18, wherein the 5' end suppression sequence is at least 10 nucleotides in length.

20. The assay of any one of paragraphs 16-19, wherein the longer amplification product generated in step (d) is at least 40 nucleotides in length.

21. The assay of any one of paragraphs 16-20, wherein the extending of the hybridized reverse primer using the 5' to 3' polymerase that lacks 5' to 3' exonuclease activity and substantially lacks strand displacement activity of step (d) occurs for at least 5 seconds or more.

22. The assay of any one of paragraphs 16-21, wherein the forward selective primer further comprises a loop spacer sequence, wherein said loop spacer sequence is 5' of the 3' end priming sequence and does not comprise a sequence complementary to the complementary extension sequences.

23. The assay of paragraph 22, wherein the loop spacer sequence is at least 3 nucleotides in length.

24. The assay of any one of paragraphs 16-23, wherein the reverse primer is a reverse selective primer.

25. The assay of paragraph 24, wherein the reverse selective primer targets a different suppression target sequence than the forward selective primer.

26. The assay of any one of paragraphs 16-25, wherein the nucleic acid sample is a DNA sample.

27. The assay of any one of paragraphs 16-26, wherein the forward selective primer comprises one or more locked nucleic acids (LNAs).

28. The assay of any one of paragraphs 16-27, wherein the 5' suppression sequence of the forward selective primer comprises one or more locked nucleic acids (LNAs).

29. The assay of any one of paragraphs 16-28, wherein the assay is a cancer screening assay.

30. The assay of any one of paragraphs 16-28, wherein the assay is a personalized cancer recurrence detection assay.

31. The assay of any one of paragraphs 29 or 30, wherein the amplification target sequence comprises a mutation or epigenetic modification found in cancer cells.

32. The assay of any one of paragraphs 29-31, wherein the nucleic acid sample is obtained from a blood, serum, plasma, or urine sample.

33. The assay of any one of paragraphs 16-28, wherein the assay is an autism screening assay.

34. The assay of any one of paragraphs 16-28, wherein the assay is a prenatal genetic detection assay.

35. The assay of any one of paragraphs 16-28, wherein the assay is a microbial detection assay.

36. A kit for detecting the presence of one of two or more variants of a nucleic acid sequence in a nucleic acid sample, the kit comprising: at least one forward selective primer, the forward selective primer comprising: (i) a 3' end priming sequence that is fully complementary and hybridizes to a portion of an amplification target sequence and a suppression target sequence, and (ii) a 5' end suppression sequence that is substantially identical to a portion of the suppression target sequence, such that the portion of the suppression target to which the 5' suppression sequence is substantially identical is 5' of the portion of the suppression target sequence to which the 3' end priming sequence hybridizes; and instructions and packaging materials thereof.

37. The kit of paragraph 36, further comprising a reverse primer specific for a sequence complementary to both the amplification target sequence and the suppression target sequence.

38. The kit of paragraph 36, further comprising a reverse selective primer.

39. The kit of paragraph 38, wherein the reverse selective primer targets a different suppression target sequence than the forward selective primer.

40. The kit of any one of paragraphs 36-30 further comprising a thermostable DNA polymerase lacking 5' to 3' exonuclease activity and substantially lacking strand displacement activity.

EXAMPLES

The methods, assays, and kits described herein provide approaches for the detection, identification, and/or selective amplification of specific species or variants of nucleic acid sequences within an excess of unwanted similar sequences or variants, which are actively suppressed. Accordingly, the approaches described herein provide methods of selectively amplifying and/or quantifying a target nucleic acid variant present in, or isolated from, a sample of interest, despite the presence of similar, sequence-related non-target nucleic acid variants, such as for example, a rare variant, using primers termed "nunchaku primers" or "forward selective primers."

Briefly, the methods comprise a Nunchaku Primer (NP) or forward selective primer, binding to or hybridizing to its target sequences and being extended. After a denaturing step and subsequent annealing and extension steps, the 5' suppression sequence of the forward selective primer hybridizes to a portion of the complementary sequence of the suppression target sequence (or non-target nucleic acid sequence), forming a hairpin loop. This prevents a modified polymerase without 5'-3' exonuclease activity from synthesizing a strand complementary to the complementary extension sequence to completion, thus failing to generate sequences with binding sites for both the forward selective primer and the reverse primer in subsequent rounds of amplification. Thus, the amplification product derived from the suppression target sequence or non-target sequence only amplifies cubically or quadratically, i.e., is suppressed relative to sequences that amplify exponentially. On the other hand, target amplicons or amplification target sequence amplicons, the amplification of which are not impacted by 5' suppression sequence hybridizing, do not have interference in the polymerase extension step, and thus these amplification target sequence amplicons can amplify exponentially. Embodiments of these methods are depicted in FIG. 1 and FIG. 13.

Figure 2:
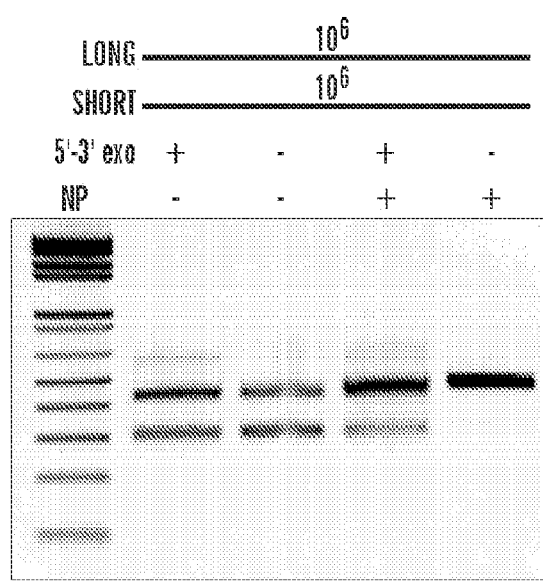
FIG. 2 demonstrates the requirement that the polymerase used in the tail-loop suppression PCR methods described herein lack 5'-3' exonuclease activity. Long and short amplicons with the same primer binding sites are amplified with a standard primer set or a primer set comprising a forward selective primer and a polymerase with 5'-3' exonuclease activity (5'-3'exo+) or without 5'-3' exonuclease activity (5'-3'exo−), and a common reverse primer. The forward selective primer (referred to as NP in the figure) is designed to suppress the amplification of short amplicons. Initial template amounts for both long and short amplicons is $10^6$ copies. The 4th column demonstrates suppression of short amplicons using a forward selective primer (NP) and a 5'-3' exonuclease negative polymerase. The 3rd column demonstrates failure of suppression with the use of a forward selective primer (NP) and a polymerase having 5' to 3' exonuclease activity.

The polymerase used in the tail-loop suppression PCR methods described herein during the extension steps is required to lack 5'-3' exonuclease activity. As demonstrated at FIG. 2, long and short amplicons with the same primer binding sites were amplified with a standard primer set or a primer set comprising a forward selective primer and a polymerase with 5'-3' exonuclease activity (5'-3'exo+) or without 5'-3' exonuclease activity (5'-3'exo−), and a common reverse primer. The forward selective primer (referred to as NP in FIG. 2) was designed to suppress the amplification of short amplicons. Initial template amounts for both long and short amplicons was $10^6$ copies. Short amplicons were suppressed using a forward selective primer (NP) and a 5'-3' exonuclease negative polymerase. In contrast, a failure of suppression activity was observed with the use of a forward selective primer (NP) and a polymerase having 5' to 3' exonuclease activity.

The relationship between the suppression efficiency of the methods described herein and "primer distance" and PCR extension times was also examined. For example, as shown at FIG. 3C, suppression efficiency was found to drop at short primer distances (10-200 bp), except close to 0 bp. As shown at FIG. 3D, there is a relationship between extension time and suppression efficiency, and an extension time of around 15 sec for the exemplary polymerase used was optimal for suppression. Optimal extension times for other polymerases can be determined in like manner.

The relationship between suppression efficiency of the methods described herein and loop sequence sizes or spacer sequences between the 5' suppression sequence and the 3'end target-specific priming sequence of the forward selective primer was investigated. As shown at FIG. 4, it was found that the smaller the loop size, the better the suppression in the short primer distance region (~50-200 bp). This suggests, without wishing to be bound or limited by theory, that the drop in suppression efficiency when there is a short primer distance region is due to the balance between hairpin formation speed and polymerase synthesis speed.

Figure 5:
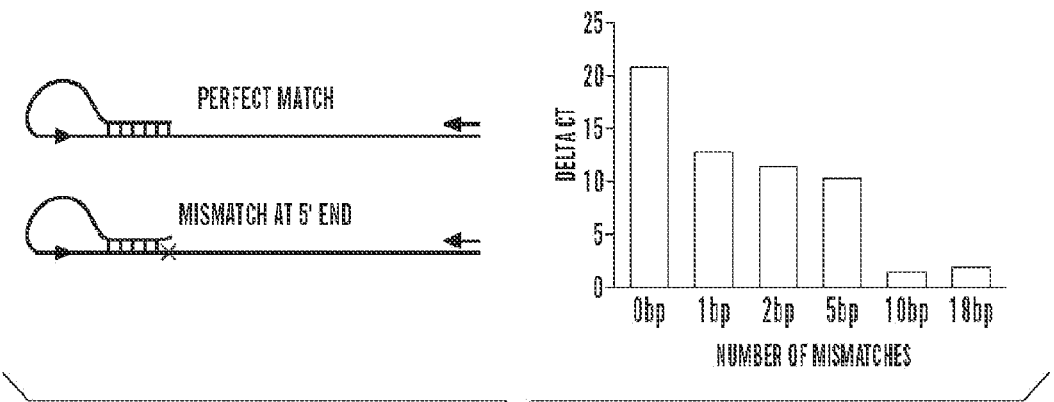
FIG. 5 demonstrates the relationship between suppression efficiency of the methods described herein and mismatches. Single base pair differences can be detected using embodiments of the methods described herein. When a SNP mismatch exists at the 5' end of the tail, the polymerase lacking 5' to 3' exonuclease activity can open the hybridized tail-loop sequence or 5' suppression sequence and eliminate or at least partially overcome the suppressive effect. The difference between no-mismatch (0 bp in the figure) and single by mismatch demonstrates the applicability of the methods described herein to SNP (single nucleotide polymorphism) detection.

The relationship between suppression efficiency of the methods described herein and mismatches was examined, and it was found that single base pair differences can be detected using embodiments of the methods described herein. When a SNP mismatch exists at the 5' end of the tail, the polymerase lacking 5' to 3' exonuclease activity can open the hybridized tail-loop sequence or 5' suppression sequence and eliminate or at least partially overcome the suppressive effect. The difference between no-mismatch (0 bp in FIG. 5) and single by mismatch demonstrates the applicability of the methods described herein to SNP (single nucleotide polymorphism) detection.

Figure 6:
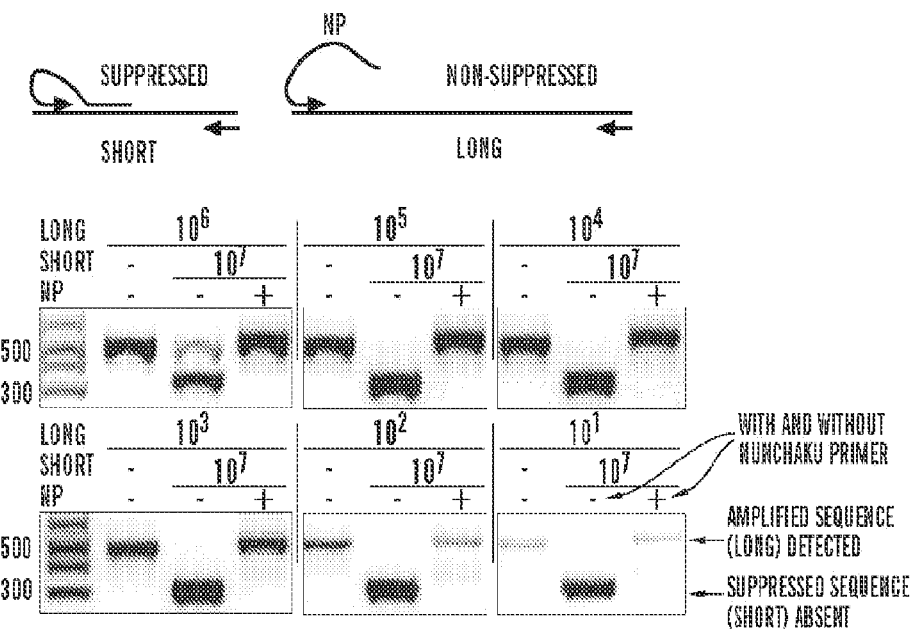
FIG. 6 demonstrates complete million-fold suppression using an embodiment of the methods described herein. The upper panel illustrates a long amplicon and short amplicon comprising the same primer binding sites being amplified. The long amplicon and short amplicons have a varying ratio of starting copy number. In the lower panel: Top row left block: Left lane: $10^6$ copies of the long amplicon (500 bp) is amplified using standard primers. Middle lane: $10^6$ copies of long amplicon and $10^7$ copies of short amplicons (300 bp) are amplified with standard primers. Right lane: starting material is same for the middle lane but one of the standard primers is replaced with a forward selective primer (labeled NP in the figure) targeted against the short amplicon. The other blocks are similar except for differing starting copy number for the long amplicon. The left most lanes are size ladders.

The ability of the methods described to suppress amplification even when the sequences to be suppressed are in vast excess is demonstrated at FIG. 6, which shows complete million-fold suppression using an embodiment of the methods described herein.

Figure 7:
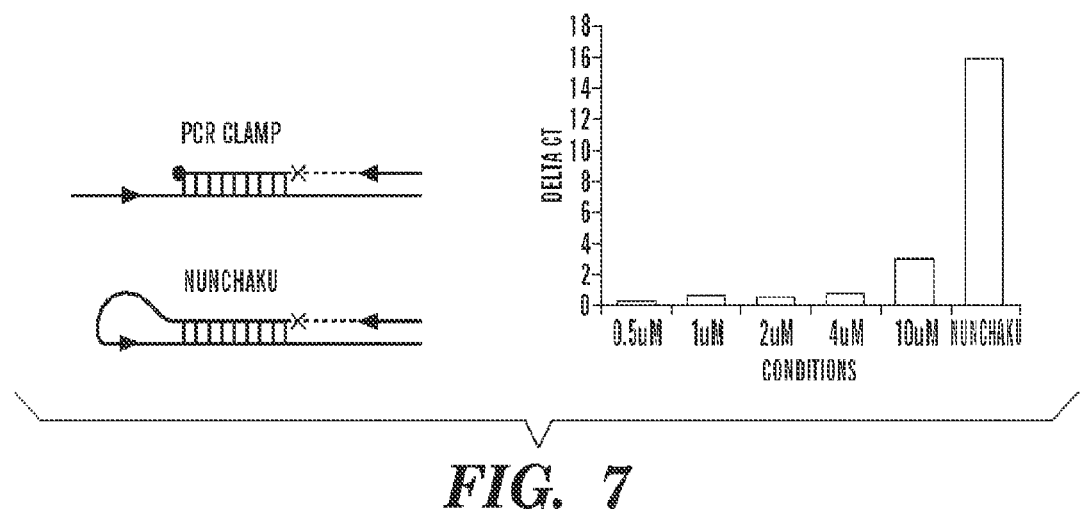
FIG. 7 shows a comparison of suppression efficiency using an embodiment of the methods described herein with the PCR clamp method. The exact same primer binding sites and template sequences were used. The suppression target sequence (clamp oligo or 5'-tail of a forward selective primer) was also the same for the comparison purpose. (Right panel) Suppression delta Ct's are plotted against concentration of the clamp oligo added (0.5 uM to 10 uM) in the PCR-clamp method or using an embodiment of the methods described herein (Nunchaku primer).
Figure 8:
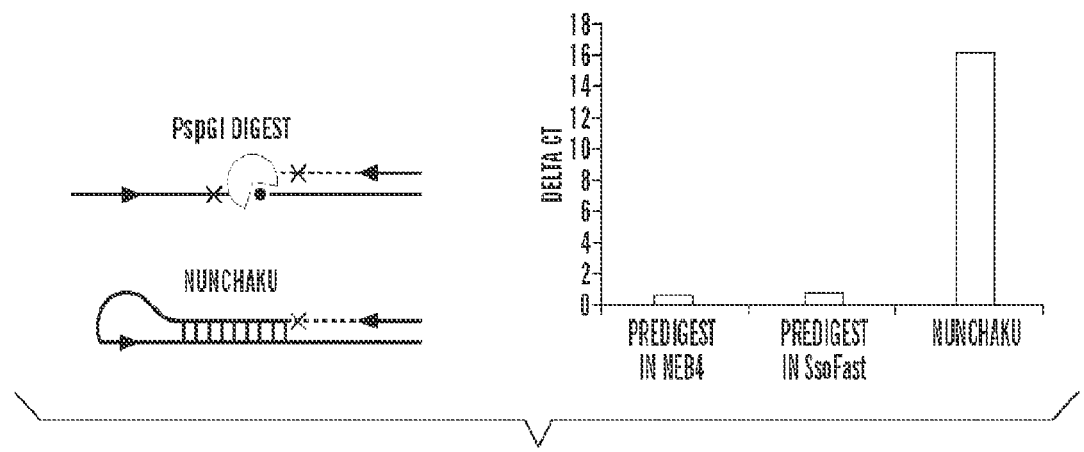
FIG. 8 shows a comparison of suppression efficiency using an embodiment of the methods described herein with the restriction enzyme-based method. Primer binding sites and template sequences were exactly the same between PspGI based suppression and the suppression based on the method described herein for comparison purposes. Template was first digested in either NEB4 buffer (left column) or in PCR mix (middle column) preceding to PCR reaction for PspGI based method.
Figure 9:
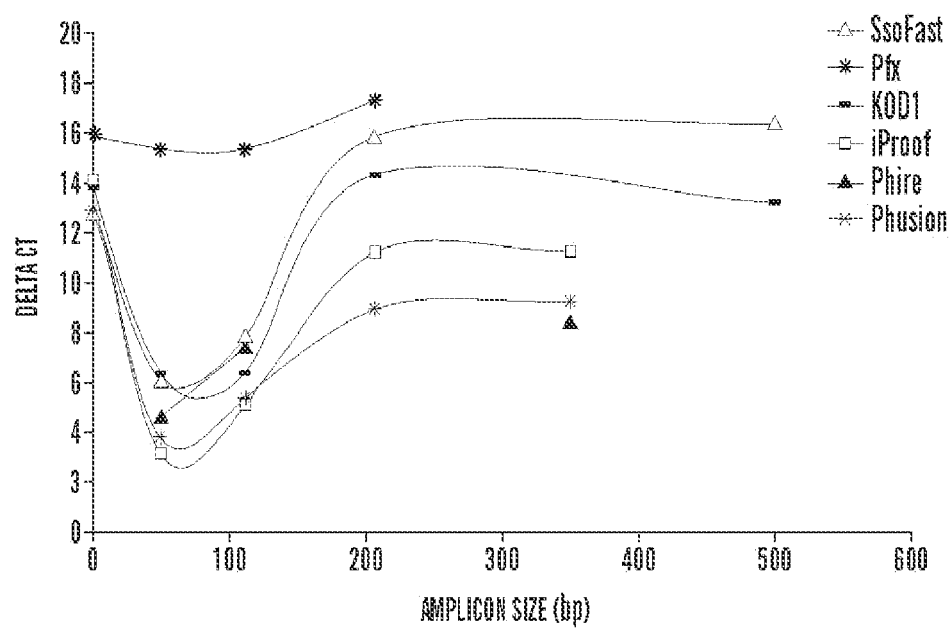
FIG. 9 demonstrates the relationship between suppression efficiency of the methods described herein and various polymerases.

Suppression efficiency using an embodiment of the methods described herein was compared with the PCR clamp method at FIGS. 7 and 14. In FIG. 7, the exact same primer binding sites and template sequences were used. The suppression target sequence (clamp oligo or 5'-tail of a forward selective primer) was also the same for the comparison purpose. Suppression capability was measured as the difference in cycle number in real time PCR, as demonstrated herein. In addition, suppression efficiency using an embodiment of the methods described herein was compared with a restriction enzyme-based method at FIGS. 8 and 14. In FIG. 8, primer binding sites and template sequences were exactly the same between PspGI based suppression and the suppression based on the method described herein for comparison purposes. It was found that whether compared to PCR clamping or to restriction enzyme based suppression methods, the tail-loop PCR methods described herein had greatly increased suppression capability—approximately $2^9$ times better than the restriction enzyme technique (~500×) and $2^{13}$ times better than the PCR clamp technique (~8000×).

Figure 10:
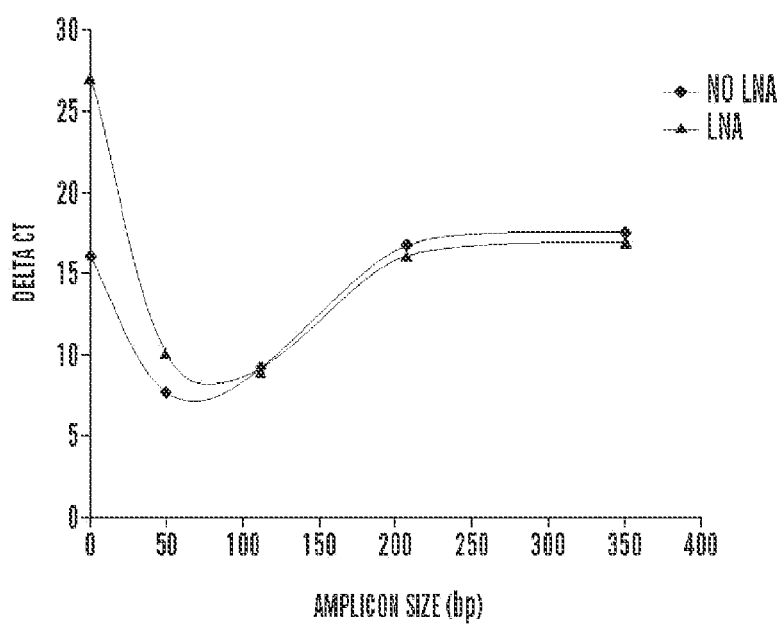
FIG. 10 demonstrates that using Locked Nucleic Acids (LNA) in some embodiments of the methods described herein improves suppression efficiency in those embodiments of the methods described herein where short primer distances are used, especially at 0 bp primer distance.

The effects of using locked nucleic acids (LNAs) in the methods described herein were also examined. For example, as shown at FIG. 10, improved suppression efficiency was observed when locked nucleic acids were used in those embodiments of the methods described herein where short primer distances were used, especially, for example, at 0 bp primer distance.

Figure 11:
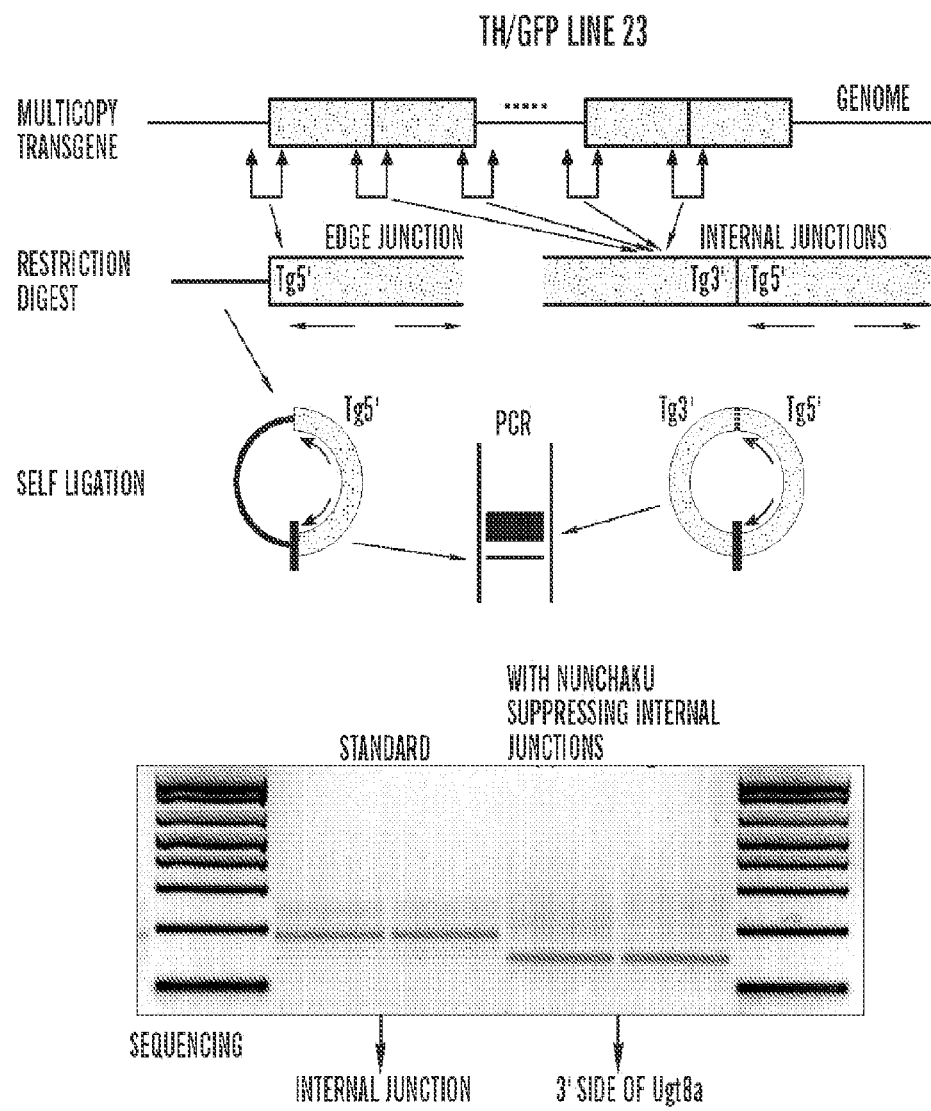
FIG. 11 demonstrates an application of the methods described herein in performing multicopy transgene localization by inverse PCR.
Figure 12:
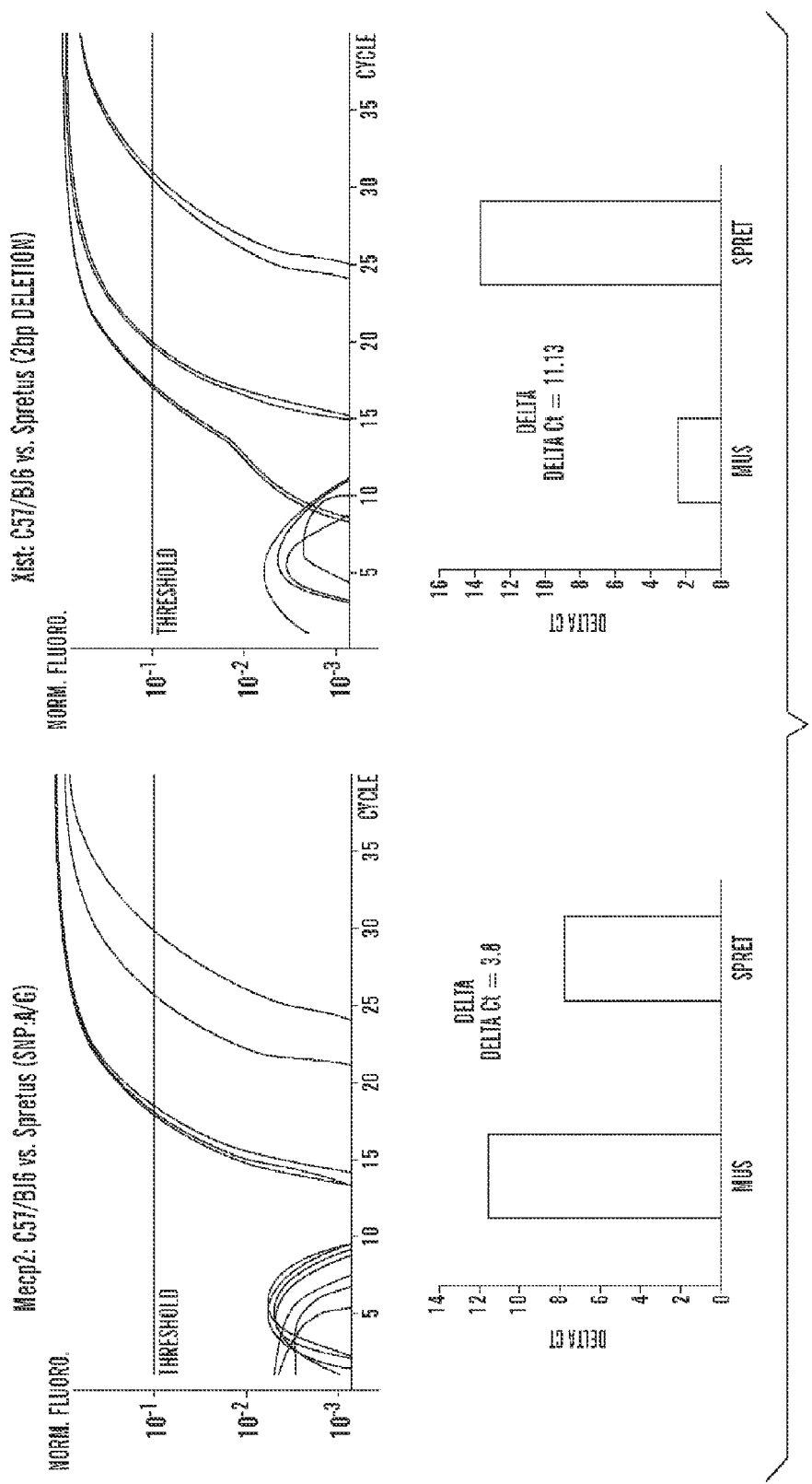
FIG. 12 demonstrates detection of a SNP and a 2-bp deletion for Mecp2 and Xist respectively between C57/BJ6 and Spretus mouse strains using an embodiment of the methods described herein.

The applicability of the methods described herein in performing multicopy transgene localization by inverse PCR is shown at FIG. 11. The ability of the methods described herein to detect single nucleotide polymorphisms and small deletion is shown at FIG. 12, which demonstrates detection of a SNP and a 2-bp deletion for Mecp2 and Xist respectively between C57/BJ6 and Spretus mouse strains using an embodiment of the methods described herein.

Application of the tail-loop suppression PCR methods described herein in the prevention of amplification of unwanted dimer formation and inserted carrier sequences during the construction of a library of sequences, such as a library of microRNA sequences, was also examined, as illustrated at FIG. 15.

We claim:
1. A method of selectively amplifying one of two or more variants of a nucleic acid sequence in a nucleic acid sample, the method comprising:
(a) hybridizing a forward selective primer to a nucleic acid sample comprising an amplification target sequence and a suppression target sequence, wherein the forward selective primer comprises: (i) a 3' end priming sequence that is complementary to and hybridizes to a portion of the amplification target sequence and the suppression target sequence, and (ii) a 5' end suppression sequence that is substantially identical to a portion of the suppression target sequence, wherein the portion of the suppression target to which the 5' suppression sequence is substantially identical is 5' of the portion of the suppression target sequence to which the 3' end priming sequence hybridizes;
(b) extending the hybridized forward selective primer of step (a) using a polymerase enzyme, the extension generating hybridized duplexes comprising: (i) the amplification target sequence and a hybridized complementary extension sequence, wherein the complementary extension sequence comprises, in the 5' to 3' direction, the forward selective primer and a sequence complementary to the amplification target sequence, and (ii) the suppression target sequence and a hybridized complementary extension sequence, wherein the complementary extension sequence comprises, in the 5' to 3' direction, the forward selective primer and a sequence complementary to the suppression target sequence;
(c) denaturing the hybridized duplexes of step (b) to separate target sequences and complementary extension sequences; and

(d) hybridizing a reverse primer to the complementary extension sequences of step (c), and extending the hybridized reverse primer using a 5' to 3' polymerase that lacks 5' to 3' exonuclease activity and substantially lacks strand displacement activity, wherein if the complementary extension sequence comprises the sequence complementary to the suppression target sequence, then amplification is suppressed by formation of a stem loop by the 5' suppression sequence and a shorter amplification product is generated, and wherein if the complementary extension sequence comprises the sequence complementary to the amplification target sequence, then amplification is not suppressed by formation of a stem loop and a longer amplification product is generated, whereby the presence of one of two or more variants of a nucleic acid sequence is detected based on the selective amplification.

2. The method of claim 1, wherein steps (a)-(d) are repeated at least 10 times.

3. The method of claim 1, wherein the forward selective primer is at least 30 nucleotides in length.

4. The method of claim 1, wherein the longer amplification product generated in step (d) is at least 40 nucleotides in length.

5. The method of claim 1, wherein the extending of the hybridized reverse primer using the 5' to 3' polymerase that lacks 5' to 3' exonuclease activity and substantially lacks strand displacement activity of step (d) occurs for at least 5 seconds or more.

6. The method of claim 1, wherein the forward selective primer further comprises a loop spacer sequence, wherein said loop sequence is 5' of the 3' end priming sequence and does not comprise a sequence complementary to the complementary extension sequences.

7. The method of claim 1, wherein the reverse primer is a reverse selective primer.

8. The method of claim 1, wherein the forward selective primer comprises one or more locked nucleic acids (LNAs).

9. The method of claim 1, wherein the 5' suppression sequence of the forward selective primer comprises one or more locked nucleic acids (LNAs).

10. An assay for selectively amplifying one of two or more variants of a nucleic acid sequence in a nucleic acid sample, the assay comprising:
(a) hybridizing a forward selective primer to a nucleic acid sample comprising an amplification target sequence and a suppression target sequence, wherein the forward selective primer comprises: (i) a 3' end priming sequence that is complementary to and hybridizes to a portion of the amplification target sequence and the suppression target sequence, and (ii) a 5' end suppression sequence that is at least 90% identical to a portion of the suppression target sequence, wherein the portion of the at least one suppression target to which the 5' suppression sequence is at least 90% identical is 5' of the portion of the suppression target sequence to which the 3' end priming sequence hybridizes;
(b) extending the hybridized forward selective primer of step (a) using a polymerase enzyme, the extension generating hybridized duplexes comprising: (i) the amplification target sequence and a hybridized complementary extension sequence, wherein the complementary extension sequence comprises, in the 5' to 3' direction, the forward selective primer and a sequence complementary to the amplification target sequence, and (ii) the suppression target sequence and a hybridized complementary extension sequence, wherein the complementary extension sequence comprises, in the 5' to 3' direction, the forward selective primer and a sequence complementary to the suppression target sequence;
(c) denaturing the hybridized duplexes of step (b) to separate target sequences and complementary extension sequences; and
(d) hybridizing a reverse primer to the complementary extension sequences of step (c), and extending the hybridized reverse primer using a 5' to 3' polymerase that lacks 5' to 3' exonuclease activity and substantially lacks strand displacement activity, wherein if the complementary extension sequence comprises the sequence complementary to the suppression target sequence, then amplification is suppressed by formation of a stem loop by the 5' suppression sequence and a shorter amplification product is generated, and wherein if the complementary extension sequence comprises the sequence complementary to the amplification target sequence, then amplification is not suppressed by formation of a stem loop and a longer amplification product is generated, whereby the presence of one of two or more variants of a nucleic acid sequence is detected based on the selective amplification.

11. The assay of claim 10, wherein steps (a)-(d) are repeated at least 10 times.

12. The assay of claim 10, wherein the forward selective primer is at least 30 nucleotides in length.

13. The assay of claim 10, wherein the longer amplification product generated in step (d) is at least 40 nucleotides in length.

14. The assay of claim 10, wherein the extending of the hybridized reverse primer using the 5' to 3' polymerase that lacks 5' to 3' exonuclease activity and substantially lacks strand displacement activity of step (d) occurs for at least 5 seconds or more.

15. The assay of claim 10, wherein the forward selective primer further comprises a loop spacer sequence, wherein said loop spacer sequence is 5' of the 3' end priming sequence and does not comprise a sequence complementary to the complementary extension sequences.

16. The assay of assay of claim 10, wherein the assay is selected from a cancer screening assay, an autism screening assay, a prenatal genetic detection assay, and amicrobial detection assay.

17. The assay of assay of claim 10, wherein the amplification target sequence comprises a mutation or epigenetic modification found in cancer cells.

* * * * *

UNITED STATES PATENT AND TRADEMARK OFFICE
CERTIFICATE OF CORRECTION

Page 1 of 1

PATENT NO. : 9,518,292 B2
APPLICATION NO. : 14/119471
DATED : December 13, 2016
INVENTOR(S) : Ken Sugino et al.

It is certified that error appears in the above-identified patent and that said Letters Patent is hereby corrected as shown below:

In the Specification

Column 1, Lines 16-19 should read:
This invention was made with government support under MH078844 awarded by the National Institutes of Health. The government has certain rights in the invention.

Signed and Sealed this
Sixth Day of November, 2018

Andrei Iancu
*Director of the United States Patent and Trademark Office*